US007291616B2

(12) United States Patent
Bhatt et al.

(10) Patent No.: US 7,291,616 B2
(45) Date of Patent: Nov. 6, 2007

(54) ARYL TRIAZINES AS LPAAT-β INHIBITORS AND USES THEREOF

(75) Inventors: Rama Bhatt, Shoreline, WA (US); Baoqing Gong, Shoreline, WA (US); Feng Hong, Seattle, WA (US); Scott A. Jenkins, Seattle, WA (US); J. Peter Klein, Vashon, WA (US); Anil M. Kumar, Puyallup, WA (US); John Tulinsky, Seattle, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 598 days.

(21) Appl. No.: 10/285,364

(22) Filed: Oct. 30, 2002

(65) Prior Publication Data

US 2003/0153570 A1   Aug. 14, 2003

Related U.S. Application Data

(60) Provisional application No. 60/330,772, filed on Oct. 31, 2001.

(51) Int. Cl.
*A61K 31/53* (2006.01)
*C07D 251/48* (2006.01)

(52) U.S. Cl. ............... 514/245; 544/206; 544/216; 514/241

(58) Field of Classification Search ............ 544/206, 544/216; 514/241, 245
See application file for complete search history.

(56) References Cited

U.S. PATENT DOCUMENTS

| 3,119,823 | A | * | 1/1964 | Shapiro et al. ............. 544/206 |
| 3,933,814 | A |   | 1/1976 | Haberkorn et al. ...... 260/248 NS |
| 3,948,893 | A |   | 4/1976 | Aichinger et al. ...... 260/248 NS |
| 3,966,725 | A |   | 6/1976 | Reisdorff et al. ...... 260/248 NS |
| 4,219,552 | A |   | 8/1980 | Haberkorn et al. ......... 424/247 |
| 4,499,269 | A |   | 2/1985 | Bennion et al. ............ 544/198 |
| 5,102,927 | A |   | 4/1992 | Rody et al. ................ 524/100 |
| 5,260,362 | A |   | 11/1993 | Rody et al. ................ 524/100 |
| 5,545,836 | A |   | 8/1996 | Reinehr et al. ............ 544/216 |
| 5,702,717 | A |   | 12/1997 | Cha et al. .................. 424/425 |
| 5,856,331 | A |   | 1/1999 | Bursten ..................... 514/263 |
| 5,962,453 | A | * | 10/1999 | Ueda et al. ................. 514/245 |
| 6,004,985 | A |   | 12/1999 | Kochanny et al. ........ 514/341 |
| 6,150,360 | A |   | 11/2000 | Daeyaert et al. ........ 514/236.2 |
| 6,150,362 | A |   | 11/2000 | Henkin et al. ............. 514/245 |
| 6,150,382 | A |   | 11/2000 | Kochanny et al. ........ 514/341 |
| 6,166,014 | A |   | 12/2000 | Kochanny et al. ........ 514/241 |
| 6,193,960 | B1 |   | 2/2001 | Metzger et al. ............ 424/59 |
| 6,288,228 | B1 |   | 9/2001 | Henkin et al. ............. 544/197 |

FOREIGN PATENT DOCUMENTS

| DE | 1200314 |   | 9/1965 |
| DE | 2226474 | * | 2/1973 |
| EP | 525 262 A1 |   | 2/1993 |
| EP | 0525262 A1 | * | 5/1993 |
| FR | 1321624 |   | 3/1963 |
| GB | 0963814 | * | 1/1962 |
| JP | 48-28486 |   | 4/1973 |
| JP | 49-69688 |   | 7/1974 |
| SU | 274102 |   | 4/1970 |
| WO | WO91/11465 |   | 8/1991 |
| WO | WO 00/25780 |   | 5/2000 |
| WO | WO-00/25780 A1 | * | 5/2000 |
| WO | WO 01/25220 |   | 4/2001 |
| WO | WO 01/25220 A1 | * | 4/2001 |
| WO | WO 02/36578 |   | 5/2002 |

OTHER PUBLICATIONS

Cecil Textbook of Medicine, edited by Bennet, J.C., and Plum F., 20th edition,vol. 1, 1004-1010, 1996.*
Hasan et al. Expert Opin. Bio. Ther. 1(4): 703-718, 2001.*
Pergram et al. Semin. Oncol. 3 Suppl 11: 29-37, 2002.*
Koizumi et al., Nippon Noyaku Gakaishi 19(2), 85-92, 1994, CA 121: 157609, 1994.*
Elkafrawy et al., Phosphorus, Sulfur and Silicon and the Related Elements 62(1-4),275-279, 1991, CA 115: 279963, 1991.*
Moussa et al., Journal of Chemical Society of Pakistan 11(3), 194-199, 1989, CA 113: 59112, 1990.*
Yuki et al., Kobunshi Ronbunshu 40(11), 739-744, 1984, CA 100: 103965, 1984.*
Seo et al., Kobunshi Ronbunshu 31(6), 401-405, 1974, CA 81: 169925, 1974.*
Murai et al., JP 49069688, CA 81: 136188, 1974.*
Ohto et al., Bulletin of the Chemical Society of Japan 47(5), 1301-1302, 1974, CA 81: 37076, 1974.*
Yuki et al., Nagoya Kogyo Daigaku Gakuho 24, 423-427, 1972, CA 81: 403898, 1974.*
Yuki et al., Nippon Kagaku Kaishi 1, 103-107, 1974, CA 80: 82903, 1974.*
Michalik et al., Wissenschaftliche Zeitschrift der Universitaet Rostock, Mathematisch Naturwissenschaftliche Reihe 21(2), 101-111, 1972, CA 79: 18680, 1973.*
Masuda et al., JP 48028486, CA 78: 159683, 1973.*
Yuki et al., Bulletin of the Chemical Society of Japan 44(9), 2444-2447, 1971, CA 75: 151765, 1971.*
Yuki et al., Bulletin of the Chemical Society of Japan 43(7), 2130-2134, 1970, CA 73: 56484, 1970.*
Fomenko et al., Vysokomolekulyarnye Soedineniya Seriya B: Kratkie Soobshcheniya 11 (5), 387-390, 1969, CA 71: 39618, 1969.*
Burmistrov et al., SU 162150, CA 61: 47941, 1964.*
Bonham et al., Expert Opin. Ther. Targets 7(5): 643-661, 2003.*
Brodskii et al., "The mechanism underlying the action of secondary aromatic amine- type antioxidants and their ether on the radiation oxidation of N-butylpropionamide and polycaproamide," *Chemical Abstracts*, Accession No. 69:3284, 1968.
Budesinsky et al., "Substituted 2,4-diamino-6-phenyl-1,3,5-triazines," *Chemical Abstracts*, Accession No. 97:6328, 1982.

(Continued)

*Primary Examiner*—Venkataraman Balasubramanian
(74) *Attorney, Agent, or Firm*—Seed IP Law Group PLLC

(57) ABSTRACT

The invention relates to aryl triazines and uses thereof, including to inhibit lysophosphatidic acid acyltransferase β (LPAAT-β) activity and/or proliferation of cells such as tumor cells.

2 Claims, No Drawings

OTHER PUBLICATIONS

Burmistrov et al., "6-Amino-4-arylamino-2-(o-hydroxyphenyl) triazines," *Chemical Abstracts*, Accession No. 61:47941, 1964.

Chen, C. et al., "A Convenient Synthetic Method for Trisubstituted s-Triazines," *Chemical Abstracts*, Accession No. 124:146076, 1995.

Elkafrawy, A.F. et al., "Synthesis and reaction of some 4-aryl-2-benzylthio-1, 6-dihydro-6-thiono-1,3,5-triazines," *Chemical Abstracts*, Accession No. 115:279963, 1991.

Michalik, M. et al., "Synthesis of nitrogen-containing heterocycles," *Chemical Abstracts*, Accession No. 79:18680, 1973.

Moussa, G.E.M. et al., "Some reactions on 4-aryl-2-substituted amino-1,6-dihydro-6-thioxo-1,3,5 triazines," *Chemical Abstracts*, Accession No. 113:59112, 1990.

Shapiro, S.L. et al., "Guanamines. VIII. 6-(Substituted-phenyl) guanamines," *Chemical Abstracts*, Accession No. 56:60602, 1962.

Yuki, Y. et al., "Preparation of amino-s-triazines with amino or nitrophenyl groups," *Chemical Abstracts*, Accession No. 75:151765, 1971.

Moolenaar, W.H., "Lysophosphatidic Acid, a Multifunctional Phospholipid Messenger," *Journal of Biological Chemistry* 270(22): 12949-12952, Jun. 2, 1995.

Xu et al, "Lysophospholipids activate ovarian and breast cancer cells," *Biochemical Journal* 309: 933-940, Aug. 1, 1995.

Imamura et al, "Induction of in vitro tumor cell invasion of cellular monolayers by lysophosphatidic acid or phospholipase D," *Biochemical and Biophysical Research Communications* 193(2): 497-503, Jun. 15, 1993.

Bursten et al., "Lipid A activation of glomerular mesangial cells: mimicry of the bioactive lipid, phophatidic acid," *American Journal of Physiology* 262(2): C328-C338, Feb. 1992.

Bursten et al., "Interleukin-1 Rapidly Stimulates Lysophosphatidate Acyltransferase and Phosphatidate Phosphohydrolase Activities in Human Mesangial Cells," *Journal of Biological Chemistry* 266(31): 20732-20743, Nov. 5, 1991.

Kester, M., "Platelet-Activating Factor Stimulates Phosphatidic Acid Formation in Cultured Rat Mesangial Cells: Roles of Phospholipase D, Diglyceride Kinase, and De Novo Phospholipid Synthesis," *Journal of Cellular Physiology* 156: 317-325, 1993.

English, D., "Phosphatidic acid: A lipid messenger involved in intracellular and extracellular signaling," *Cell Signal* 8(5): 341-347, 1996.

Martin et al., "Increased concentrations of phosphatidate diacylglycerol and ceramide in *ras*- and tyrosine kinase (*fps*)-transformed fibroblasts," *Oncogene* 14(13):1571-1580, Apr. 3, 1997.

Rizzo et al., "The Recruitment of Raf-1 to Membranes Is Mediated by Direct Interaction with Phosphatidic Acid and Is Independent of Association with Ras," *Journal of Biological Chemistry* 275(31): 23911-23918, Aug. 4, 2000.

Stamps et al., "A human cDNA sequence with homology to non-mammalian lysophosphatidic acid acyltransferases," *Biochemical Journal* 326:455-461, Sep. 1, 1997.

Kume and Shimizu, "cDNA Cloning and Expression of Murine 1-Acyl-*sn*-glycerol-3-phosphate Acyltransferase," *Biochemical and Biophysical Research Communications* 237(3): 663-666, Aug. 28, 1997.

West et al., "Cloning and Expression of Two Human Lysophosphatidic Acid Acyltransferase cDNAs That Enhance Cytokine-Induced Signaling Responses in Cells," *DNA and Cell Biology* 16(6): 691-701, Jun. 1997.

Eberhardt et al., "Human Lysophosphatidic Acid Acyltransferase," *Journal of Biological Chemistry* 272(32): 20299-20305, Aug. 8, 1997.

Leung et al., "Molecular Cloning of Two Alternatively Spliced Forms of Human Phosphatidic Acid Phosphatase cDNAs that Are Differentially Expressed in Normal and Tumor Cells," *DNA and Cell Biology* 17(4): 377-385, Apr. 1998.

Fong and Engleman, "Dendritic Cells in Cancer Immunotherapy," *Annual Review of Immunology* 18: 245-273, 2000.

Schreurs et al., "Dendritic Cell-Based Vaccines: From Mouse Models to Clinical Cancer Immunotherapy," *Critical Reviews in Oncogenesis* 11(1): 1-17, 2000.

Miller and Rosman, "Improved Retroviral Vectors for Gene Transfer and Expression," *BioTechniques* 7(9): 980-EOA, Oct. 1989.

Hoess and Abremski, "The Cre-*lox* Recombination System," *Nucleic Acids and Molecular Biology* 4: 99-109, 1990.

Sauer, B., "Inducible Gene Targeting in Mice Using the Cre/*lox* System," *Methods: A Companion to Methods in Enzymology* 14(4): 381-392, Apr. 1998.

Wetmur and Davidson, "Kinetics of Renaturation of DNA," *Journal of Molecular Biology* 31(3): 349-370, Feb. 14, 1968.

Sharp et al., "Viral DNA in Transformed Cells. I. A Study of the Sequences of Adenovirus 2 DNA in a Line of Transformed Rat Cells Using Specific Fragments of the Viral Genome," *J. Mol. Biol.* 86(4): 709-726, Jul. 15, 1974.

Britten and Kohne, "Repeated Sequences in DNA," *Science* 161(3841): 529-540, Aug. 9, 1968.

Sutton, W.D., "A crude nuclease preparation suitable for use in DNA reassociation experiments," *Biochimica et Biophysica Acta* 240(4): 522-531, Jul. 29, 1971.

Köhler and Milstein, "Continuous cultures of fused cells secreting antibody of predefined specificity," *Nature* 256: 495-497, Aug. 7, 1975.

Losman et al., "Baboon anti-idiotype antibodies mimic a carcinoembryonic antigen epitope," *Int. J. Cancer* 46(2): 310-314, Aug. 15, 1990.

Orlandi et al., "Cloning immunoglobulin variable domains for expression by the polymerase chain reaction," *Proc. Natl. Acad. Sci. USA* 86(10): 3833-3837, May 1989.

Pitts et al., "Rapid Synthesis of Triazine Inhibitors of Inosine Monophosphate Dehydrogenase," *Bioorganic & Medicinal Chemistry Letters* 12: 2137-2140, 2002.

Sluka et al., "2,4-diamino-6-phenyl-1,3,5-triazines," *Collection Czechoslov. Chem. Commun.* 43: 1639-1646, 1978.

* cited by examiner

ARYL TRIAZINES AS LPAAT-β INHIBITORS AND USES THEREOF

CROSS-REFERENCE TO RELATED APPLICATION

This application claims the benefit of U.S. Provisional Patent Application No. 60/330,772 filed Oct. 31, 2001, where this provisional application is incorporated herein by reference in its entirety.

BACKGROUND of THE INVENTION

1. Field of the Invention

The invention is in the field of organic and medicinal chemistry. In particular, the invention relates to aryl triazines and uses thereof, such as inhibiting the activity of lysophosphatidic acid acyltransferase β (LPAAT-β) activity and/or inhibiting the proliferation of a cell (e.g., tumor cell).

2. Description of the Related Art

Lysophosphatidic acid acyltransferase (LPAAT) catalyzes the acylation of lysophosphatidic acid (LPA) to phosphatidic acid. LPA is the simplest glycerophospholipid, consisting of a glycerol molecule, a phosphate group, and a fatty acyl chain. LPAAT adds a second fatty acyl chain to LPA, producing phosphatidic acid (PA). PA is the precursor molecule for certain phosphoglycerides, such as phosphatidylinositol, and diacylglycerols, which are necessary for the production of other phosphoglycerides, such as phosphatidylcholine, and for triacyiglycerols, which are essential biological fuel molecules.

In addition to being a crucial precursor molecule in biosynthetic reactions, LPA has been added to the list of intercellular lipid messenger molecules. LPA interacts with G protein-coupled receptors, coupling to various independent effector pathways including inhibition of adenylate cyclase, stimulation of phospholipase C, activation of MAP kinases, and activation of the small GTP-binding proteins Ras and Rho. Moolenaar, *J. Biol. Chem* 28:1294 (1995). The physiological effects of LPA have not been fully characterized as yet. However, one of the physiological effects that is known is that LPA promotes the growth and invasion of tumor cells. It has been shown that the addition of LPA to ovarian or breast cancer cell lines induces cell proliferation, increases intracellular calcium levels, and activates MAP kinase. Xu et al., *Biochem. J.* 309:933 (1995). In addition, LPA has been shown to induce MM1 tumor cells to invade cultured mesothelial cell monolayers. Imamura et al., *Biochem. Biophys. Res. Comm.* 193:497 (1993).

Like LPA, PA is also a messenger molecule. PA is a key messenger in a common signaling pathway activated by proinflammatory mediators such as interleukin-1β, tumor necrosis factor α, platelet activating factor, and lipid A. Bursten et al., *Am. J. Physiol.* 262:C328 (1992); Bursten et al., *J. Biol. Chem.* 255:20732 (1991); Kester, *J. Cell Physiol.* 156:317 (1993). PA has been implicated in mitogenesis of several cell lines [English, Cell Signal 8:341 (1996)]. PA level has been found to be increased in either ras or fps transformed cell lines compared to the parental Rat2 fibroblast cell line [Martin et al., *Oncogene* 14:1571 (1997)]. Activation of Raf-1, an essential component of the MAPK signaling cascade, by extracellular signals is initiated by association with intracellular membranes. Recruitment of Raf-1 to membranes has been reported to be mediated by direct association with phosphatidic acid [Rizzo et al., *J. Biol. Chem.* 275:23911-8 (2000)]. Thus, LPAAT, as an enzyme that regulates PA content in cells, may play a role in cancer, and may also mediate inflammatory responses to various proinflammatory agents.

LPAAT exists in a LPAAT-α form and a LPAAT-β form. Northern blot analysis shows that LPAAT-α is expressed in all human tissues tested with the highest expression level found in skeletal muscle (West et al., *DNA Cell Biol.* 16:691 (1997)). The uniformity of LPAAT-α expression has also been found in additional tissues such as prostate, testis, ovary, small intestine, and colon (Stamps et al., *Biochem. J.* 326:455 (1997)) as well as in mouse tissues (Kume et al., *Biochem. Biophys. Res. Commun.* 237:663 (1997)). A 2 kb and a 1.3 kb forms, possibly due to alternative utilization of polyadenylation signals at the 3'-UTR, have been found in murine LPAAT-α mRNA (Kume et al., *Biochem. Biophys. Res. Commun* 237:663 (1997)), whereas only one major human LPAAT-α mRNA of 2 kb in size has been detected by Northern analysis. West et al., *DNA Cell Biol.* 16:691 (1997); Stamps et al., *Biochem. J.* 326:455 (1997).

In contrast, LPAAT-β demonstrates a distinct tissue distribution of mRNA expression. West et al., *DNA Cell Biol.* 16:691 (1997). LPAAT-β is most highly expressed in liver and heart tissues. LPAAT-β is also expressed at moderate levels in pancreas, lung, skeletal muscle, kidney, spleen, and bone marrow; and at low levels in thymus, brain and placenta. This differential pattern of LPAAT-β expression has been confirmed independently (Eberhardt et al., *J. Biol. Chem.* 272:20299 (1997)) with the only discrepancy being that high level, instead of moderate level, of LPAAT-β has been detected in pancreas, possibly due to slight lot variations in commercial RNA blots (Clontech, Palo Alto, Calif.). In addition, moderate LPAAT-β expression has been found in prostate, testis, ovary, small intestine, and colon with the small intestine containing relatively higher amounts. Eberhardt et al., *J Biol Chem* 272:20299 (1997). Within various brain sections, high expression has been found in the subthalamic nucleus and spinal cord; and least in the cerebellum, caudate nucleus, corpus callosum, and hippocampus. LPAAT-β can also be detected in myeloid cell lines THP-1, HL-60, and U937 with the mRNA levels remaining the same with or without phorbal-ester treatment. The size difference between human LPAAT-α and LPAAT-β mRNA is consistent with the sequence data, in which LPAAT-α has a longer 3'-UTR. The differential tissue expression pattern LPAAT-α and LPAAT-β mRNA would suggest these two genes are regulated differently and are likely to have independent functions. Therefore, a desirable feature in compounds that inhibit LPAAT activity is that they are specific in inhibiting one isoform of the enzyme over the other (i.e., LPAAT-β over LPAAT-α).

LPAAT-β mRNA has been found to be elevated in tumor tissues (e.g., uterus, fallopian tube, and ovary), as compared to its expression in the corresponding normal tissues. However, no significant difference was found in LPAAT-α mRNA level between the various tumor tissues and the normal adjacent tissues. In two of the tumor tissues (fallopian tube and ovary) where LPAAT-α mRNA was elevated, PAP2-α mRNA expression was found to be suppressed, as it was also in tumors of the colon, rectum, and breast. Thus, LPAAT-β (rather than LPAAT-α) appears to be a relevant target for inhibition.

There is a need in the art for improved compositions and methods. The present invention fills this need, and further provides other related advantages.

BRIEF SUMMARY OF THE INVENTION

Briefly stated, the present invention provides a variety of compounds and uses thereof. More specifically, the compounds of the present invention are triazines that possess aromatic substituents which are directly or indirectly attached to two carbons of the triazine ring. The compounds are generally of the formula:

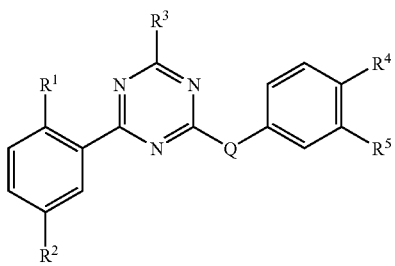

where $R^1$-$R^5$ are hydrogen or non-hydrogen substituents, and Q is a heteroatom or heteroatom attached to one or more methylene groups. In preferred embodiments of compounds of the present invention:

Q is NH, N—$(CH_2)_n$, $(CH_2)_n$—N, O, O—$(CH_2)_n$, $(CH_2)_n$—O, S, S—$(CH_2)_n$ or $(CH_2)_n$—S, where n is 1-10;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, $CCl_3$, C≡N, $NH_2$, or SR where R and R' independently are alkyl;

$R^4$ and $R^5$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+(=O)O^-$, C≡N, $N_3$, SH, SR where R is alkyl, $NH_2$, NHR or NRR' where R and R' independently are alkyl or are joined together to form a ring with the N, or $R^4$ and $R^5$ are taken together with the benzene ring to form a heterocycle or $R^4$ and $R^5$ are independently alkyl or alkenyl and joined together to form a ring with the two carbon atoms of the benzene ring to which $R^4$ and $R^5$ are attached; and with the proviso that $R^1$ and $R^2$ are not both Cl where $R^3$ is $NH_2$ and Q is N;

with the proviso that $R^4$ and $R^5$ are not both H;

with the proviso that $R^4$ is not $OCH_3$ or t-butyl where $R^1$ is Cl, $R^2$ is H, $R^3$ is H, $R^5$ is NH and Q is NH;

with the proviso that where one of $R^4$ or $R^5$ is H, the other is not $CH_3$, $OCH_3$, Cl, Br or $NO_2$ where $R^1$ is OH or $OCH_3$, $R^2$ is Cl, $R^3$ is $NH_2$ and Q is NH;

with the proviso that $R^4$ and $R^5$ are not joined together to form naphthalene with the benzene ring to which $R^4$ and $R^5$ are attached where $R^1$ is $OCH_3$ or $CH_2OH$, $R^2$ is Cl, $R^3$ is $NH_2$ and Q is NH.

A compound or salt thereof as described above may be combined with a pharmaceutical carrier or diluent to form a pharmaceutical composition of the present invention.

A compound, salt thereof or pharmaceutical composition of the present invention, as well as other aryl triazines (or salts or pharmaceutical compositions thereof), may be used in one or more methods and medical devices of the present invention. In one method, the activity of LPAAT-β may be reduced by the step comprising contacting LPAAT-β with a compound or salt thereof, or in combination with a phar-maceutically acceptable carrier or diluent, in an amount effective to reduce LPAAT-β activity, wherein the compound has the formula:

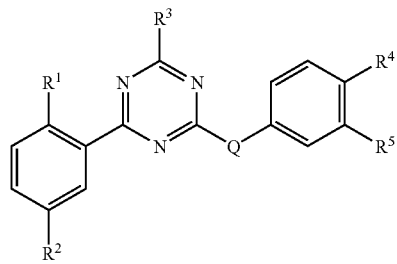

wherein:

Q is NH, N—$(CH_2)_n$, $(CH_2)_n$—N, O, O—$(CH_2)_n$, $(CH_2)_n$—O, S, S—$(CH_2)_n$ or $(CH_2)_n$—S, where n is 1-10;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, Cl, $CCl_3$, C≡N, $NH_2$, NHR, NRR' or SR where R and R' independently are alkyl, or R and R' are joined together to form a ring with the N;

$R^4$ and $R^5$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+(=O)O^-$, C≡N, $N_3$, SH, SR where R is alkyl, $NH_2$, NHR or NRR' where R and R' independently are alkyl or are joined together to form a ring with the N, or $R^4$ and $R^5$ are taken together with the benzene ring to form a heterocycle or $R^4$ and $R^5$ are independently alkyl or alkenyl and joined together to form a ring with the two carbon atoms of the benzene ring to which $R^4$ and $R^5$ are attached; and with the proviso that $R^1$ and $R^2$ are not both Cl where $R^3$ is $NH_2$ and Q is N.

In another method, the proliferation of a cell in which the activity of LPAAT-β is required for the proliferation of the cell may be inhibited by the step comprising contacting the cell with a compound or salt thereof, or in combination with a pharmaceutically acceptable carrier or diluent, in an amount effective to inhibit the proliferation of the cell, wherein the compound has the formula:

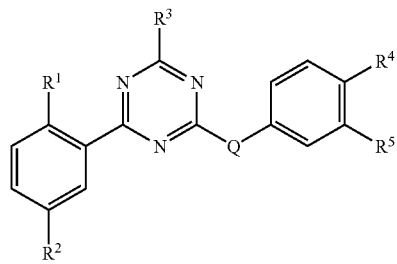

wherein:

Q is NH, N—$(CH_2)_n$, $(CH_2)_n$—N, O, O—$(CH_2)_n$, $(CH_2)_n$—O, S, S—$(CH_2)_n$ or $(CH_2)_n$—S, where n is 1-10;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, Cl, $CCl_3$, C≡N, $NH_2$, NHR, NRR' or SR where R and R' independently are alkyl, or R and R' are joined together to form a ring with the N;

$R^4$ and $R^5$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+(=O)O^-$, C≡N, $N_3$, SH, SR where R is alkyl, $NH_2$, NHR or NRR' where R and R' independently are alkyl or are joined together to form a ring with the N, or $R^4$ and $R^5$ are taken together with the benzene ring to form a heterocycle or $R^4$ and $R^5$ are independently alkyl or alkenyl and joined together to form a ring with the two carbon atoms of the benzene ring to which $R^4$ and $R^5$ are attached; and with the proviso that $R^1$ and $R^2$ are not both Cl where $R^3$ is $NH_2$ and Q is N.

In a further method, the treatment of a cancer in which LPAAT-β activity is associated may be effected by the step comprising administering to an animal in need, a compound or salt thereof, or in combination with a pharmaceutically acceptable carrier or diluent, in an amount effective to treat the cancer, wherein the compound has the formula:

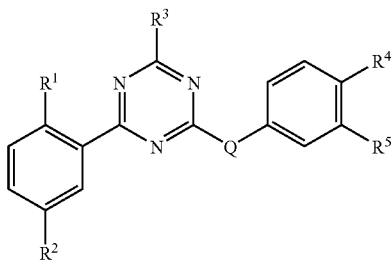

wherein:

Q is NH, N—$(CH_2)_n$, $(CH_2)_n$—N, O, O—$(CH_2)_n$, $(CH_2)_n$—O, S, S—$(CH_2)_n$ or $(CH_2)_n$—S, where n is 1-10;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, Cl, $CCl_3$, C≡N, $NH_2$, NHR, NRR' or SR where R and R' independently are alkyl, or R and R' are joined together to form a ring with the N;

$R^4$ and $R^5$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+(=O)O^-$, C≡N, $N_3$, SH, SR where R is alkyl, $NH_2$, NHR or NRR' where R and R' independently are alkyl or are joined together to form a ring with the N, or $R^4$ and $R^5$ are taken together with the benzene ring to form a heterocycle or $R^4$ and $R^5$ are independently alkyl or alkenyl and joined together to form a ring with the two carbon atoms of the benzene ring to which $R^4$ and $R^5$ are attached; and with the proviso that $R^1$ and $R^2$ are not both Cl where $R^3$ is $NH_2$ and Q is N.

Also provided is a coated medical device for inhibiting the proliferation of a cell in which the activity of LPAAT-β is required for the proliferation of the cell comprising a medical device coated with a compound or salt thereof, or in combination with a pharmaceutically acceptable carrier or diluent, in an amount effective to inhibit the proliferation of the cell, wherein the compound has the formula:

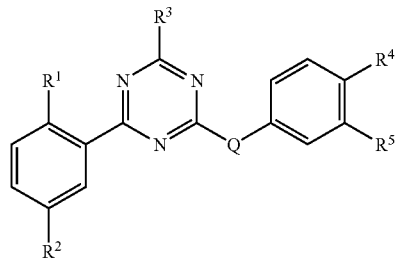

wherein:

Q is NH, N—$(CH_2)_n$, $(CH_2)_n$—N, O, O—$(CH_2)_n$, $(CH_2)_n$—O, S, S—$(CH_2)_n$ or $(CH_2)_n$—S, where n is 1-10;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, Cl, $CCl_3$, C≡N, $NH_2$, NHR, NRR' or SR where R and R' independently are alkyl, or R and R' are joined together to form a ring with the N;

$R^4$ and $R^5$ are independently H, OH, alkyl, alkenyl, alkynyl, alkoxy, $(CH_2)_n$—OR where R is H or alkyl and n is 1-10, Cl, F, Br, $CR_3$ where $R_3$ is $Cl_3$, $F_3$ or $Br_3$, acyl, heterocycle, $N^+(=O)O^-$, C≡N, $N_3$, SH, SR where R is alkyl, $NH_2$, NHR or NRR' where R and R' independently are alkyl or are joined together to form a ring with the N, or $R^4$ and $R^5$ are taken together with the benzene ring to form a heterocycle or $R^4$ and $R^5$ are independently alkyl or alkenyl and joined together to form a ring with the two carbon atoms of the benzene ring to which $R^4$ and $R^5$ are attached; and with the proviso that $R^1$ and $R^2$ are not both Cl where $R^3$ is $NH_2$ and Q is N.

These and other aspects of the present invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

In the present description, the term "alkyl" refers to straight- or branched-chain hydrocarbons having from 1 to 10 carbon atoms and more preferably 1 to 8 carbon atoms which include, by way of example, methyl, ethyl, n-propyl, i-propyl, n-butyl, t-butyl and the like. The alkyl group may be substituted or unsubstituted. When substituted, the substituted group(s) is preferably one or more independently selected from alkyl, cycloalkyl, heteroalicyclic, aryl, heteroaryl, haloalkyl, halo, hydroxy, alkoxy, mercapto, cyano, sulfonamidyl, aminosulfonyl, acyl, acyloxy, and substituted amino.

"Alkenyl" includes monovalent hydrocarbon radicals having straight, cyclic, or branched moieties, and combinations thereof which comprise at least one carbon-carbon double bond. The alkenyl group may be substituted or unsubstituted. When substituted, the substituted group(s) is preferably one or more independently selected from alkyl, acyl, cycloalkyl, heteroalicyclic, aryl, haloalkyl, alkoxy and substituted amino.

"Alkoxy" refers to the group "—O-alkyl" which includes, by way of example, methoxy, ethoxy, n-propoxy, i-propoxy, n-butoxy, t-butoxy and the like. It further refers to the group "—O-alkyl-W-alkyl" where W is O or N; for example, —O—$(CH_2)_n$—W—$(CH_2)_m$ where n and m are independently 1-10.

"Substituted amino" denotes the group —NRR, wherein each R group is independently selected from hydrogen, acyl, alkyl, cycloalkyl, aryl, or the R groups can be joined together with the nitrogen to form a heterocyclic ring (e.g., piperidine, piperazine, or a morpholine ring).

"Aryl" refers to an unsaturated aromatic carbocyclic group of 6 to 14 carbon atoms having a single ring (e.g., phenyl) or multiple condensed rings (e.g., naphthyl or anthryl). The aryl group may be unsubstituted or substituted; in the latter case, the substituent or substituents preferably are selected independently from alkyl, aryl, haloalkyl, halo, hydroxy, alkoxy, mercapto, cyano, sulfonamidyl, aminosulfonyl, acyl, acyloxy, nitro, and substituted amino.

"Heteroaryl" is a monocyclic or fused ring (i.e., rings which share an adjacent pair of atoms) group having in the ring(s) one or more atoms selected preferably from nitrogen, oxygen and sulfur and, in addition, having a completely conjugated π-electron system. Exemplary heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more independently selected from alkyl, aryl, haloalkyl, halo, hydroxy, alkoxy, mercapto, cyano, sulfonamidyl, aminosulfonyl, acyl, acyloxy, nitro and substituted amino.

"Cycloalkyl" encompasses cyclic alkyl groups that contain between 3 and 8 carbon atoms and have a single cyclic ring, illustrated by cyclopropyl, cyclobutyl, cyclopentyl, and cyclooctyl. The cycloalkyl ring may be substituted or unsubstituted.

Again, a substituted cycloalkyl ring carries one or more substituent groups, independently selected preferably from alkyl, aryl, haloalkyl, halo, hydroxy, alkoxy, mercapto, cyano, sulfonamidyl, aminosulfonyl, acyl, acyloxy, vitro, and substituted amino.

"Heteroalicyclic" refers to a monocyclic or fused ring group having in the ring(s) one or more atoms selected preferably from nitrogen, oxygen and sulfur. The rings may also have one or more double bonds. However, the rings do not have a completely conjugated i-electron system. The heteroalicyclic ring may be substituted or unsubstituted. When substituted, the substituted group(s) preferably are selected independently from alkyl, aryl, haloalkyl, halo, hydroxy, alkoxy, mercapto, cyano, sulfonamidyl, aminosulfonyl, acyl, acyloxy, vitro, and substituted amino.

"Halogen" or "halo" refers to fluoro, chloro, bromo, iodo.

"Acyl" group refers to the C(O)—R" group, where R" is selected preferably from hydrogen, hydroxy, alkyl, haloalkyl, cycloalkyl, aryl optionally substituted with one or more alkyl, haloalkyl, alkoxy, halo and substituted amino groups, heteroaryl (bonded through a ring carbon) optionally substituted with one or more alkyl, haloalkyl, alkoxy, halo and substituted amino groups and heteroalicyclic (bonded through a ring carbon) optionally substituted with one or more alkyl, haloalkyl, alkoxy, halo and substituted amino groups. Acyl groups include aldehydes, ketones, acids, acid halides, esters and amides. Preferred acyl groups are carboxy groups, e.g., acids and esters. Esters include amino acid ester derivatives. The acyl group may be attached to a compound's backbone at either end of the acyl group, i.e., via the C or the R".

The phrase "physiologically acceptable salt" refers to those salts that retain the biological effectiveness and properties of the particular compound. Physiologically acceptable salts are often useful because they may have improved stability and/or solubility in pharmaceutical compositions over the free base form of the compound. A physiologically acceptable salt may be obtained by reaction of a free base with an inorganic acid such as hydrochloric acid, hydrobromic acid, nitric acid, phosphoric acid, sulfuric acid, and perchloric acid and the like, or with an organic acid such as acetic acid, oxalic acid, malic acid, maleic acid, methanesulfonic acid, ethanesulfonic acid, p-toluenesulfonic acid, salicylic acid, tartaric acid, citric acid, succinic acid or malonic acid, and the like. A physiologically acceptable salt may also be obtained by reaction of a free acid with a base such as sodium, potassium or lithium hydroxide, bicarbonate or carbonate, and the like.

As noted above, the present invention provides aryl triazines, physiologically acceptable salts thereof and uses thereof. The triazines possess aromatic substituents that are directly or indirectly attached to two carbons of the aryl triazine ring. The compounds are generally of the formula:

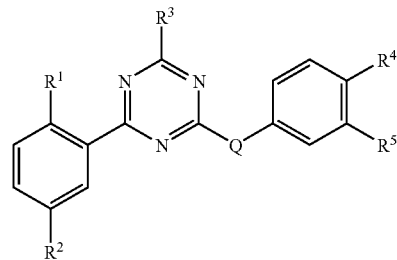

where $R^1$-$R^5$ are hydrogen or non-hydrogen substituents, and Q is a heteroatom or heteroatom attached to one or more methylene groups.

Preferred embodiments of a compound of the present invention, or a compound only for the methods and medical devices of the present invention where the compound was previously known, include the following selections for the general formula above. Preferred embodiments include where Q is a heteroatom (preferably N, O or S) and may be attached to one or more methylene groups to provide additional spacing between the triazine ring and the phenyl ring possessing $R^4$ and $R^5$. Where there are one or more methylene groups, the heteroatom may be oriented such that it is attached directly to the triazine ring or attached directly to the phenyl ring possessing $R^4$ and $R^5$. For example, Q may be N—$(CH_2)_n$, $(CH_2)_n$—N, O—$(CH_2)_n$, $(CH_2)_n$—O, S—$(CH_2)_n$ or $(CH_2)_n$—S, where n is typically 1-10. Particularly preferred is where Q is NH.

Preferred embodiments include where $R^1$ is H, OH, alkyl, alkoxy, halogen (preferably Cl, F or Br), $CR_3$, $NH_2$, NHR or NRR'. $R_3$ of $CR_3$ is (halo)$_3$, preferably $Cl_3$, $F_3$ or $Br_3$. R and R' of NHR and NRR' are independently alkyl. The term "independently," as used throughout, refers to independent selection of a group, but does not exclude the possibility that two groups are identical. For example, the alkyl group of R and R' of NRR' may be the same or different. Particularly preferred is where $R^1$ is alkyl, alkoxy or Cl.

Preferred embodiments include where $R^2$ is H, OH, alkyl, alkoxy, halogen (preferably Cl, F or Br), or $CR_3$. $R_3$ of $CR_3$ is (halo)$_3$, preferably $Cl_3$, $F_3$ or $Br_3$. Particularly preferred is where $R^2$ is Cl.

Preferred embodiments include where $R^3$ is H, alkyl, alkoxy, halogen (preferably Cl), $CR_3$, C≡N, $NH_2$, NHR, NRR' or SR. $R_3$ of $CR_3$ is (halo)$_3$, preferably $Cl_3$. R of SR is alkyl. R and R' of NHR and NRR' are independently alkyl, or R and R' are joined together to form a ring with the N. Examples of such rings include piperidine, piperazine and morpholine. Particularly preferred is where $R^3$ is alkyl or $NH_2$.

Preferred embodiments include where $R^4$ and $R^5$ are independently H, OH, alkyl, alkenyl, alkynyl, alkoxy, $(CH_2)_n$—OR, halogen (preferably Cl, F or Br), $CR_3$, acyl, heterocycle, $N^+(=O)O^-$, C≡N, $N_3$, SH, SR, $NH_2$, NHR or NRR'. R of $(CH_2)_n$—OR is H or alkyl, and n is typically 1-10, with $CH_2$—OH and $(CH_2)_2$—OH preferred. $R_3$ of $CR_3$ is (halo)$_3$, preferably $Cl_3$, $F_3$ or $Br_3$. A preferred heterocycle is oxazol. A preferred acyl is phenone (so forms benzophenone when taken with the benzene ring to which it is attached) or ester, such as an amino acid ester derivative. R of SR is alkyl. R and R' of NHR and NRR' are independently alkyl, or R and R' are joined together to form a ring with the N. Examples of such rings include piperidine, piperazine and morpholine. Particularly preferred is where $R^4$ or $R^5$ is Cl, Br, $(CH_2)_2$—OH, $N^+(=O)O^-$ or C≡N. Also preferred is where $R^4$ or $R^5$ is a non-polar substituent, e.g., alkyl. Alternatively, $R^4$ and $R^5$ may be taken together with the benzene ring to form a heterocycle. A preferred heterocycle is indazolyl, benzotriazolyl, indolyl, benzothiazolyl, benzimidazolyl or benzodioxolyl. Particularly preferred is where $R^4$ and $R^5$ are taken together with the benzene ring to form indazole. Alternatively, $R^4$ and $R^5$ are independently alkyl or alkenyl, and are joined together to form a ring with the two carbon atoms of the benzene ring to which $R^4$ and $R^5$ are attached. A preferred ring is where $R^4$ and $R^5$ are taken together with the benzene ring to form indane.

Particularly preferred compounds of the present invention, or for use in the methods or medical devices of the present invention, are one or more of those shown in Table 1 of Example 91 below, and physiologically acceptable salts thereof.

It may be advantageous for certain uses to enhance the solubility and/or bioavailability of one or more of the compounds. This may be accomplished, for example, by the addition of one or more substituents to the compound. For example, the addition of hydrophilic groups, such as hydroxyl groups, may be advantageous. Other substituents for enhancing solubility and/or bioavailability include amino acids (e.g., polyglutamate or polylysine), di-peptides, polymers (e.g., PEG or POG), monocarboxylic acids (e.g., hemi-succinate), and esters. Any group that enhances solubility and/or bioavailability of a compound may be used, provided that the group does not significantly impair the relevant biological property of the compound.

It may be advantageous for certain uses to prepare a compound (or physiologically acceptable salt thereof as a "prodrug." As used herein, the term "compound" encompasses a prodrug form of the parent compound. "Prodrug" herein refers to a chemical substance that is converted into the parent compound in vivo. Prodrugs often are useful because, in some situations, they may be easier to administer than the parent compound. They may, for instance, be bioavailable by oral administration whereas the parent compound is not. The prodrug may also have improved solubility in pharmaceutical compositions over the parent compound. An example of a prodrug would be a parent compound of the present invention which is administered as an ester (the "prodrug") to facilitate transmittal across a cell membrane where water solubility is detrimental to mobility. The ester is then metabolically hydrolyzed to the carboxylic acid, the active entity, once inside the cell where water solubility is beneficial. Such a prodrug is generally inactive (or less active) until converted to the active form.

Pharmaceutical compositions of the compounds of the present invention and the physiologically acceptable salts thereof are preferred embodiments of this invention. Pharmaceutical compositions of the compounds and salts thereof of the present invention may be manufactured by processes well known in the art; e.g., by means of conventional mixing, dissolving, granulating, dragee-making, levigating, emulsifying, encapsulating, entrapping or lyophilizing processes.

Pharmaceutical compositions may be formulated in a conventional manner using one or more physiologically acceptable carriers or diluents. Proper formulation is generally dependent upon the route of administration chosen. The aryl triazines of the present invention may be formulated such that the formulation comprises a single aryl triazine or a mixture of two or more aryl triazines described herein. Alternatively, one or more aryl triazines may be formulated with one or more other agents which are active for a general or specific disease, disorder or condition.

For injection, the compounds of the invention may be formulated as sterile aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with physiologically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be made with the use of a solid carrier or diluent, optionally grinding the resulting mixture, and processing the mixture of granules, after adding suitable auxiliaries, if desired, to obtain tablets or dragee cores. Suitable carriers or diluents are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the embodiments of the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoro-ethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include sterile aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation (see, for example, U.S. Pat. No. 5,702,717 for a biodegradable depot for the delivery of a drug). Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The pharmaceutical compositions herein also may comprise suitable solid or gel phase carriers or diluents. Examples of such carriers or diluents include but are not limited to calcium carbonate, calcium phosphate, various sugars, starches, cellulose derivatives, gelatin, and polymers such as polyethylene glycols.

The compounds may be provided as physiologically acceptable salts wherein the compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartarate, maleate, succinate, etc. formed by the reaction of an amino group with the appropriate acid.

As noted above, LPAAT-β appears to play a role in various cellular pathways that have a connection to various diseases, disorders or conditions. The disclosure of the present invention shows unexpectedly that the aryl triazines set forth above inhibit the activity of LPAAT-β. This surprising inhibition is also specific for LPAAT-β, as the compounds tested showed weak to no inhibitory activity for LPAAT-α. In particular, none of the compounds tested for LPAAT-α had an $IC_{50}$ of less than 40 μM. In one use of the compounds of the present invention as well as other aryl triazines (collectively "compounds of the present disclosure", excluding any particular aryl triazines previously known and used for the same specific purpose), the activity of LPAAT-β is reduced. The method comprises contacting LPAAT-β with a compound or salt thereof or composition of the present disclosure in an amount effective to reduce the LPAAT-β activity. The LPAAT-β to be contacted may reside in a cell-free preparation or in intact cells, including cells within an animal.

In the context of the present invention, the term "animal" refers to any animal, including humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc), as well as feral or wild animals, including such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term. A preferred animal within the present invention is a mammal, with humans particularly preferred.

In another use of the compounds of the present disclosure, the proliferation of a cell (in which the activity of LPAAT-β is required for the proliferation of the cell) is inhibited. The method comprises contacting the cell with a compound or salt thereof or composition of the present disclosure in an amount effective to inhibit the proliferation of the cell. The cell to be contacted may be in vitro or in vivo in an animal. An example of a cell whose proliferation it is desirable to inhibit is a tumor cell. However, there are other diseases, disorders and conditions with cell types other than tumor cells for which it may be desirable to inhibit proliferation of the cell. In the context of the present invention, the term "inhibiting" refers to both total inhibition and partial inhibition (i.e., the inhibition need not be 100%).

In another use of the compounds of the present disclosure, a cancer (in which LPAAT activity is associated) is treated. Examples of cancer include prostate, breast, lung, ovarian, brain, cervical, colon or bladder cancer. The method comprises administering to an animal in need, a compound or salt thereof or composition of the present disclosure in an amount effective to treat the cancer. In the context of the present invention, the term "treating a cancer" refers to any of a variety of positive effects from the treatment, including preventing the spread of a tumor, arresting tumor growth at a primary site, eradicating the tumor, relieving a symptom associated with the cancer, or prolonging the survival time of the animal treated. For example, as used herein, treating a cancer may have the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, (4) relieving to some extent (or, preferably, eliminating) one or more symptoms associated with the cancer, and/or (5) prolonging the survival time of the recipient. In addition, treatment further includes preventing tumor occurrence or recurrence. The method may further comprise inclusion of one or more other agents for treating a cancer. Alternatively, the method may be used in conjunction with one or more other cancer therapies, such as radiation, surgery or other chemotherapy.

Suitable routes of administration may include, without limitation, oral, rectal, transmucosal or intestinal administration or intramuscular, subcutaneous, intramedullary, intrathecal, direct intraventricular, intravenous, intraperitoneal or intranasal injections.

Alternately, one may administer the compound or composition in a local rather than systemic manner, for example, via injection of the compound or composition directly into a solid tumor, often in a depot or sustained release formulation.

Furthermore, one may administer the compound or composition in a targeted drug delivery system, for example, in a liposome coated with tumor-specific antibody. The liposomes will be targeted to and taken up selectively by the tumor.

Compounds and compositions suitable for use in the methods of the present invention are compounds and compositions wherein the active ingredients are contained in an amount effective to achieve its intended purpose. Determination of an effective amount is well within the capability of those skilled in the art, especially in light of the detailed disclosure provided herein.

For any compound or composition used in the methods of the invention, the effective amount or dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of LPAAT-β activity). Such information can be used to more accurately determine useful doses in humans.

Toxicity and therapeutic efficacy of the compounds described herein can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see e.g., Fingl, et al., in "The Pharmacological Basis of Therapeutics," (1975), Chapter 1, pp. 1).

Dosage amount and interval may be adjusted individually to provide plasma levels of the active moiety which are sufficient to maintain LPAAT-β inhibitory effects, or minimal effective concentration (MEC). The MEC will vary for each compound but can be estimated from in vitro data; e.g., the concentration necessary to achieve 50-90% inhibition of LPAAT-β using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The amount of compound or composition administered will, of course, be dependent on the subject being treated, on the subject's weight, the severity of the affliction, the manner of administration and the judgment of the prescribing physician. An exemplary systemic daily dosage is about 5 to about 200 mg/kg of body weight. Normally, from about 10 to about 100 mg/kg of body weight of the compounds of the present invention, in one or more dosages per day, is effective to obtain the desired results. One of ordinary skill in the art can determine the optimal dosages and concentrations of the compounds of the preferred embodiments of the present invention with only routine experimentation.

The compounds of the present invention when used are substantially pure and preferably sterile. The phrase "substantially pure" encompasses compounds created by chemical synthesis or compounds substantially free of chemicals which may accompany the compounds in the natural state, as evidenced by thin layer chromatography (TLC) or high performance liquid chromatography (HPLC).

A compound or salt thereof of the present disclosure, or pharmaceutical composition of either, may be used to coat a medical device. A variety of medical devices, such as a stent, may be coated. The medical device may be composed of a bioadsorbable and biodegradable material. Due to the antiproliferative properties of the compounds of the present disclosure, a stent or other medical device that is coated with such a compound or salt thereof or pharmaceutical composition of either may be used for inhibiting the proliferation of a cell. The coated medical devices of the present invention may be used in a variety of ways. A preferred use is to inhibit the proliferation of tumor cells.

The following examples are offered by way of illustration and not by way of limitation.

EXAMPLES

Starting Materials Were Purchased from the Following Sources:
Aldrich Chemical Company, St Louis, Mo.
Lancaster Synthesis, Windham, N.H.
Matrix Scientific, Columbia, S.C.
Trans World Chemicals, Rockville, Md.
Avocado Research Chemicals, Heysham, Lancashire, UK
TCI America, Portland, Oreg.
Bachem Bioscience Inc, King of Prussia, Pa.
Advanced ChemTech, Louisville, Ky.

Synthesis of Compounds Used in Certain Examples Below 2,4-Dichloro-6-(5-chloro-2-methyl-phenyl)-[1,3,5]triazine To a suspension of 5-chloro-2-methylbenzoic acid (10 g, 58.6 mmol) dichloromethane (100 ml), cooled in an ice bath, was added a solution of oxalyl chloride in dichloromethane (2 M, 33 ml, 66 mmol) followed by N,N-dimethylformamide (5 drops). After stirring for 2 hours, dimethylamine hydrochloride (9.5 g, 116 mmol) was added followed by a solution of trimethylamine (25 ml, 180 mmol) in dichloromethane (100 ml) slowly. After stirring for 3 hours, the mixture was concentrated under reduced pressure and partitioned between ethyl acetate (200 ml) and hydrochloric acid (1 M, 200 ml). The organic layer was concentrated under reduced pressure to afford 2-chloro-5, N,N,-trimethyl benzamide (11.6 g, 100% yield).

A mixture of 2-chloro-5, N,N-trimethyl benzamide (7.5 g, 37.9 mmol) and phosphorus oxychloride (3.9 ml, 41.7 mmol) was heated at 100° C. for 15 minutes. After cooling to 30° C., dichloromethane (75 ml) and chlorocyanoamidine (6.4 g, 61.8 mmol), prepared according to the method described in *Zeitschrift fur Anorganishe und Allgemeine Chemie* 322:265-285 (1963), were added. After stirring for 20 hours, the mixture was treated with water (300 ml) and dichloromethane (150 ml). The organic layer was concentrated under reduced pressure. The residue was purified by flash chromatography on silica gel eluting with hexane to provide 2,4-dichloro-6-(5-chloro-2-methyl-phenyl)-[1,3,5]triazine (3.0 g, 29% yield) as a white powder. $^1$H NMR (CDCl$_3$) 8.26 (m, 1H), 7.50 (m, 1H), 7.32 (s, 1H), 2.70 (s, 3H).

Alternatively, to a mixture of magnesium (1.46 g, 60.0 mmol) and tetrahydrofuran (100 ml) was added a small crystal of iodine followed by 4-chloro-2-iodo-toluene (12.62 g, 50 mmol). The mixture was heated under gentle reflux in an argon atmosphere for 6 hours and then cooled to −78° C. A solution of cyanuric chloride (7.84 g, 42.5 mmol) in tetrahydrofuran (45 ml) was added over 25 minutes. After stirring at −78° C. for 1 hour, the mixture was slowly warmed to room temperature and stirred for 16 hours. The reaction mixture, cooled in an ice bath, was quenched by slow addition of hydrochloric acid (1 M, 15 ml). The mixture was diluted with water (150 ml) and extracted with dichloromethane (3×125 ml). The combined extracts was washed with water (150 ml), dried over sodium sulfate, and concentrated under reduced pressure. The residue was purified by flash chromatography on silica gel eluting with ethyl acetate-hexane (7:93) to provide 2,4-dichloro-6-(5-chloro-2-methyl-phenyl)-[1,3,5]triazine (10.2 g, 87% yield) as a white powder.

2,4-Dichloro-6-(5-chloro-2-ethoxy-phenyl)-[1,3,5]triazine

To a mixture of 5-chlorosalicylic acid (20.0 g, 116 mmol) and potassium carbonate (48.4 g, 350 mmol) in acetonitrile (300 ml) was added iodoethane (24.0 ml, 299 mmol). The mixture was heated under reflux for 24 hours. After cooling to room temperature, the mixture was filtered through a pad of celite under suction and the filtrate was concentrated under reduced pressure. The residue was dissolved in ethyl acetate (200 ml). The solution was washed with water (100 ml), washed with aqueous sodium hydroxide solution (1 M, 2×100 ml), dried over sodium sulfate, and concentrated under reduced pressure. The residue was dissolved in ethanol (200 ml) and a solution of sodium hydroxide (10.7 g, 268 mmol) in water (50 ml) was added. The mixture was heated under reflux for 90 minutes. After cooling to room temperature, the mixture was concentrated under reduced pressure. The residue was dissolved in water (100 ml) and the solution was washed with diethyl ether (2×50 ml). The solution was adjusted to pH 2 by the careful addition of concentrated hydrochloric acid. After 60 minutes, the solid was filtered and dried under reduced pressure to provide 5-chloro-2-ethoxybenzoic acid (20.4 g, 90% yield).

Using the method described for the synthesis of 2,4-dichloro-6-(5-chloro-2-methyl-phenyl)-[1,3,5]triazine, 5-chloro-2-ethoxybenzoic acid afforded 2,4-dichloro-6-(5-chloro-2-ethoxy-phenyl)-[1,3,5]triazine (9.5 g, 31% yield). $^1$H NMR (DMSO-d$_6$) 7.62-7.86 (m, 2H), 7.20-7.31 (m, 1H), 4.20 (m, 2H), 1.37 (m, 3H).

2,4-Dichloro-6-(2,5-dichloro-phenyl)-[1,3,5]triazine

Using the method described for the synthesis of 2,4-dichloro-6-(5-chloro-2-methyl-phenyl)-[1,3,5]triazine, 2,5-dichlorobenzoic acid afforded 2,4-dichloro-6-(2,5-dichloro-phenyl)-[1,3,5]triazine (2.2 g, 14% yield). $^1$H NMR (DMSO-d$_6$) 8.10 (s, 1H), 7.50 (m, 2H).

Alternatively, to a solution of 2,5-dichloro-iodobenzene (3.1 g, 11.4 mmol), hexamethylphosphoramide (6.6 ml) and tetrahydrofuran (20 ml), cooled to −78° C., was added a solution of tert-butyl lithium in pentane (1.7 M, 8.7 ml, 14.8 mmol) over 20 minutes. After stirring at −78° C. for 3 hours, a solution of cyanuric chloride (3.14 g, 17.1 mmol) in tetrahydrofuran (15 ml) was added over 15 minutes. After stirring at −78° C. for 1 hour, the mixture was warmed to −20° C. over 30 minutes. The reaction was quenched by slow addition of hydrochloric acid (1 M, 20 ml). The mixture was diluted with water (50 ml) and extracted with dichloromethane (3×40 ml). The combined extracts were washed with water (2×50 ml), dried over sodium sulfate, and concentrated under reduced pressure. The residue was purified by flash chromatography on silica gel eluting with dichloromethane-hexane (3:5) to provide 2,4-dichloro-6-(2,5-dichloro-phenyl)-[1,3,5]triazine (1.98 g, 59% yield).

Example 1

6-(5-Chloro-2-methoxyphenyl)-N-(4-chlorophenyl)-[1,3,5]triazine-2,4-diamine

To a suspension of 1-(4-chlorophenyl)biguanidine hydrochloride (971 mg, 3.9 mmol) in 2 M aqueous sodium hydroxide solution (9 ml) was added a solution of 2-methoxy-5-chlorobenzoyl chloride (1.41 g, 3.9 mmol) in acetone (9 ml). After stirring for 48 hours, the acetone was removed by evaporating under vacuum. The remaining mixture was acidified to pH 2 by the addition of 1 M hydrochloric acid. The solid was filtered and purified by flash chromatography on silica gel eluting with 2% methanol-dichloromethane to provide the title compound (181 mg, 13% yield). $^1$H NMR (DMSO-d$_6$) δ 9.72 (br s, 1H), 7.83 (d, J=11 Hz, 2H), 7.41-7.58 (m, 2H), 7.10-7.35 (m, 5H), 3.77 (s, 3H).

Example 2

6-(5-Chloro-2-methoxyphenyl)-N-phenyl-[1,3,5]triazine-2,4-diamine

To a mixture of 1-phenylbiguandine hydrochloride (231 mg, 1.08 mmol) and methyl 2-methoxy-5-chlorobenzoate (0.16 ml, 1.0 mmol) in absolute ethanol (5 ml) was added 21 weight % sodium ethoxide in ethanol (1.1 ml, 2.95 mmol). The mixture was heated at reflux for 21 hours. Upon cooling to room temperature the mixture was concentrated under vacuum. The residual solid was suspended in water (5 ml), filtered and purified by flash chromatography on silica gel eluting with 2% methanol-dichloromethane to provide the title compound (90 mg, 27% yield). $^1$H NMR (CDCl3) δ 7.92 (br s, 1H), 7.65 (br s, 1H), 7.49-7.55 (m, 2H), 7.23-7.35 (m, 3H), 7.02-7.09 (m, 1H), 6.84-6.88 (m, 1H), 3.84 (s, 3H).

Example 3

6-(5-Chloro-2-methoxyphenyl)-N-(4-nitrophenyl)-[1,3,5]triazine-2,4-diamine

The reaction of 1-(4-nitrophenyl)biguanidine hydrochloride with methyl 2-methoxy-5-chlorobenzoate using the method described in Example 2 provided the title compound (36 mg, 18% yield).

Example 4

6-(2,5-Dichlorophenyl)-N-(4-chlorophenyl)-[1,3,5]triazine-2,4-diamine

The reaction of 1-(4-chlorophenyl)biguanidine hydrochloride with methyl 2,5-dichlorobenzoate using the method described in Example 2 provided the title compound (70 mg, 19% yield). $^1$H NMR (DMSO-$d_6$) δ 9.84-9.90 (br, 1H), 7.84 (d, 2H), 7.70 (d, 1H), 7.52-7.62 (m, 2H), 7.37-7.45 (br, 1H), 7.32 (d, 2H).

Example 5

N-Benzo[1,3]dioxol-5-yl-6-(5-chloro-2-methoxyphenyl)-[1,3,5]triazine-2,4-diamine The reaction of methyl 5-chloro-2-methoxybenzoate and 1-(3,4-methylenedioxyphenyl)biquanidine hydrochloride using the method described in Example 2 provided the title compound (105 mg, 28% yield). $^1$H NMR (DMSO-$d_6$) δ 9.45-9.60 (br, 1H), 7.60-7.70 (br, 1H), 7.47 (dd, 1H), 7.14 (d, 1H), 7.08 (m, 1H), 6.82 (d, 1H), 5.55 (s, 2H), 3.85 (s, 3H).

Example 6

N-(4-Chlorophenyl)-6-(2-fluoro-5-methoxyphenyl)-[1,3,5]triazine-2,4-diamine

The reaction of methyl 5-fluoro-2-methoxybenzoate and 1-(4-chlorophenyl)biquanidine hydrochloride using the method described in Example 2 provided the title compound (62 mg, 18% yield). $^1$H NMR (DMSO-$d_6$) δ 9.70-9.80 (br, 1H), 7.97 (d, 2H), 7.32 (d, 2H), 7.09-7.4 (m, 5H), 3.77

Example 7

6-(5-Chloro-2-ethoxyphenyl)-N-(4-Chlorophenyl)-[1,3,5]triazine-2,4-diamine

The reaction of 1-(4-chlorophenyl)biguanidine hydrochloride with ethyl 2-ethoxy-5-chlorobenzoate using the method described in Example 2 provided the title compound (102 mg, 15% yield). $^1$H NMR (DMSO-$d_6$) δ 9.70 (br s, 1H), 7.86 (d, J=11 Hz, 2H), 7.40-7.51 (m, 2H), 7.08-7.35 (m, 5H), 4.06 (q, J=12 Hz, 2H), 1.27 (t, J=12 Hz, 3H).

Example 8

6-(5-Chloro-2-methoxyphenyl)-N-(3,4-dichlorophenyl)-[1,3,5]triazine-2,4-diamine

The reaction of 1-(3,4-dichlorophenyl)biguanidine hydrochloride with methyl 2-methoxy-5-chlorobenzoate using the method described in Example 2 provided the title compound (106 mg, 8% yield). $^1$H NMR (DMSO-$d_6$) δ 9.90 (br s, 1H), 8.30 (br s, 1H), 7.73 (d, J=15 Hz, 1H), 7.20-7.64 (m, 5H), 7.15 (d, J=14 Hz, 1H), 3.81 (s, 3H).

Example 9

6-(5-Chloro-2-methylphenyl)-N-(4-Chlorophenyl)-[1,3,5]triazine-2,4-diamine

The reaction of 1-(4-chlorophenyl)biguanidine hydrochloride with methyl 2-methyl-5-chlorobenzoate using the method described in Example 2 provided the title compound (46 mg, 6% yield). $^1$H NMR (DMSO-$d_6$) δ 9.71 (br s, 1H), 7.65-7.87 (m, 3H), 7.18-7.44 (m, 6H), 2.50 (s, 3H).

Example 10

N-2-(4-Bromophenyl)-6-(5-chloro-2-methoxyphenyl)-[1,3,5]triazine-2,4-diamine

The reaction of 1-(4-bromophenyl)biguanidine hydrochloride (4.99 g, 17.0 mmol) with methyl 5-chloro-2-methoxybenzoate (3.15 g, 15.7 mmol) using the method described in Example 2 provided the title compound (1.47 g, 23% yield). $^1$H NMR (DMSO-$d_6$) δ 9.72 (br s, 1H), 7.82 (d, J=10 Hz, 2H), 7.37-7.57 (m, 3H), 7.11-7.30 (m, 3H), 3.78 (s, 3H).

Example 11

N-2-(4-Bromophenyl)-6-(5-chloro-2-methylphenyl)-[1,3,5]triazine-2,4-diamine

The reaction of 1-(4-bromophenyl)biguanidine hydrochloride (464 mg, 1.59 mmol) with methyl 5-chloro-2-methylbenzoate (239 mg, 1.73 mmol) using the method described in Example 2 provided the title compound (46 mg, 8% yield). $^1$H NMR (DMSO-$d_6$) δ 9.72 (br s, 1H), 7.75-7.83 (m, 2H), 7.38-7.48 (m, 3H), 7.16-7.33 (m, 2H), 2.51 (s, 3H).

Example 12

N-2-(4-Bromophenyl)-6-(2,5-dichlorophenyl)-[1,3,5]triazine-2,4-diamine

The reaction of 1-(4-bromophenyl)biguanidine hydrochloride (317 mg, 1.08 mmol) with methyl 2,5-dichlorobenzoate (205 mg, 1.0 mmol) using the method described in Example 2 provided the title compound (53 mg, 13% yield). $^1$H NMR (DMSO-$d_6$) δ 9.90 (br s, 1H), 7.70-7.82 (m, 3H), 7.55-7.60 (m, 2H), 7.31-7.48 (m, 5H).

Example 13

6-(5-Chloro-2-Methyl-Phenyl)-N-(1H-Indazol-6-yl)-[1,3,5]Triazine-2,4-Diamine

The reaction of 1-(1H-indazol-6-yl)biguanidine hydrochloride (1.6 g, 6.3 mmol) with methyl 5-chloro-2-methyl benzoate (1.8 g, 9.5 mmol) using the method described in Example 2 provided the title compound (261 mg, 12% yield). $^1$H NMR (DMSO-d$_6$) δ 12.85 (br s, 1H), 9.71 (br s, 1H), 8.06 (s, 1H), 7.95 (s, 1H), 7.78 (m, 1H), 7.61-7.64 (m, 1H), 7.41-7.44 (m, 2H), 7.31-7.34 (m, 1H), 7.23 (br s, 2H), 2.54 (s, 3H).

Example 14

N-(4-Chlorophenyl)-6-(2,5-dimethylphenyl)-[1,3,5]triazine-2,4-diamine

The reaction of 1-(4-chlorophenyl)biguanidine hydrochloride (268 mg, 1.08 mmol) with methyl 2,5-dimethylbenzoate (165 mg, 1.0 mmol) using the method described in Example 2 provided the title compound (44 mg, 13% yield). $^1$H NMR (DMSO-d$_6$) δ 9.64 (br s, 1H), 7.85 (d, 2H, J=10 Hz), 7.53 (s, 1H), 7.31 (d, 2H, J=10 Hz), 7.13-7.22 (m, 4H), 2.46 (s, 3H), 2.30 (s, 3H).

Example 15

6-(5-Chloro-2-methoxyphenyl)-N-(4-fluorophenyl)-[1,3,5]triazine-2,4-diamine

The reaction of 1-(4-fluorophenyl)biguanidine hydrochloride (927 mg, 3.9 mmol) with methyl 5-chloro-2-methoxybenzoate (782 mg, 3.9 mmol) using the method described in Example 2 provided the title compound (100 mg, 7% yield). $^1$H NMR (DMSO-d$_6$) δ 9.62 (br s, 1H), 7.79-7.86 (m, 2H), 7.44-7.56 (m, 1H), 7.07-7.22 (m, 5H), 6.88-6.9-3 (m, 1H), 3.80 (s, 3H).

Example 16

N-(4-Chlorophenyl)-6-(3-chlorophenyl)-[1,3,5]triazine-2,4-diamine

The reaction of 1-(4-chlorophenyl)biguanidine hydrochloride (268 mg, 1.08 mmol) with methyl 3-chlorobenzoate (0.139 ml, 1.0 mmol) using the method described in Example 2 provided the title compound (81 mg, 24% yield). $^1$H NMR (DMSO-d$_6$) δ 9.75 (br s, 1H), 8.20-8.33 (m, 2H), 7.87 (d, 2H, J=8 Hz), 7.52-7.67 (m, 2H), 7.22-7.44 (m, 4H).

Example 17

N-(4-Chlorophenyl)-6-(2,5-dimethoxyphenyl)-[1,3,5]triazine-2,4-diamine

The reaction of 1-(4-chlorophenyl)biguanidine hydrochloride (268 mg, 1.08 mmol) with methyl 2,5-dimethoxybenzoate (195 mg, 1.0 mmol) using the method described in Example 2 provided the title compound (61 mg, 17% yield). $^1$H NMR (DMSO-d$_6$) δ 9.70 (br s, 1H), 7.88 (d, 2H, J=9 Hz), 7.31 (d, 2H, J=9 Hz), 6.96-7.27 (m, 5H), 3.75 (br s, 6H).

Example 18

Poly-(L-glutamic acid) conjugate of 4-[4-chloro-6-(5-chloro-2-methyl-phenyl)-[1,3,5]-triazin-2-ylamino]-phenyl}-methanol A mixture of the title compound of Example 41 (3.8 g, 11.1 mmol), poly-(L-glutamic acid) (21.5 g), pyridine (4.8 ml), N,N-dimethylaminopyridine (0.470 g, 3.85 mmol), N,N-dimethylformamide (300 ml), and N,N-diisopropylcarbodiimide (1.8 g, 14.2 mmol) was stirred for 6 hours. A 10% aqueous sodium chloride solution (800 ml) was added and the mixture was adjusted to pH 2.5 by the addition of 1 M hydrochloric acid. After stirring for 30 minutes, the solid was filtered, washed with water (5×200 ml), dried by lyophilization, washed with acetonitrile (4×200 ml), and dried under reduced pressure to provide the title compound (19.6 g, 77% mass balance). $^1$H NMR (TFA-d): 7.44-7.77 (m, 7H), 5.27-5.35 (m, 2H), 4.65-4.95 (br s, 1H, poly-(L-glutamic acid) backbone), 2.52-2.75 (br s, 2H, poly-(L-glutamic acid) backbone), 2.24-2.42 (br s, 1H, poly-(L-glutamic acid) backbone) 2.02-2.09(br s, 1H, poly-(L-glutamic acid) backbone). Ratios of integrals in the $^1$H NMR spectrum indicated 20% by weight of the title compound of Example 41 in this sample.

Example 19

N-Benzo[1.3]dioxol-5-yl-6-(5-chloro-2-methyl-phenyl)-[1,3,5]triazine-2,4-diamine The reaction of 1-(3,4-methylenedioxy-phenyl)-biguanidine hydrochloride and methyl 5-chloro-2-methyl-benzoate using the method described in Example 2 provided the title compound (5% yield). $^1$H NMR (DMSO-d$_6$) 9.44 (br s, 1H), 8.72 (m, 1H), 7.54 (s, 1H), 7.40 (m, 1H), 7.30 (m, 1H), 7.04-7.15 (m, 3H), 6.82 (m, 1H), 5.92 (s, 2H), 2.50 (s, 3H).

Example 20

(4-Bromo-phenyl)-[4-chloro-6-(5-chloro-2-methyl-phenyl)-[1,3,5]triazin-2-yl]-amine A mixture of 2,4-dichloro-6-(5-chloro-2-methyl-phenyl)-[1,3,5]triazine (2.5 g, 9.1 mmol), 4-bromoaniline (1.6 g, 9.3 mmol), tetrahydrofuran (60 ml), and diisopropylethylamine (1.6 ml, 9.2 mmol) was stirred for 1 hour. The solution was treated with dichloromethane (200 ml), washed with saturated aqueous sodium chloride solution (50 ml), and concentrated under reduced pressure. The residual solid was treated with hydrochloric acid (1 M, 25 ml) and stirred vigorously for 30 minutes. Filtration and drying under reduced pressure provided the title compound (3.2 g, 86% yield). $^1$H NMR (DMSO-d$_6$) 10.75-10.80 (m, 1H), 7.85-7.92 (m, 1H), 7.50-7.65 (m, 4H), 7.40 (m, 1H), 2.58 (s, 3H).

Example 21

(4-Bromo-phenyl)-[4-(5-chloro-2-methyl-phenyl)-6-methoxy-[1,3,5]triazin-2-yl-amine To a solution of the title compound of Example 20 (100 mg, 0.25 mmol) in methanol (5 ml) was added a solution of sodium methoxide in methanol (25-30%, 0.5 ml). After stirring for 72 hours, the mixture was concentrated under reduced pressure. The residue was stirred with water (20 ml). The solid was collected by filtration, washed with hexane (5 ml), and dried under reduced pressure to provide the title compound (60 mg, 59% yield). $^1$H NMR (DMSO-d$_6$) 10.40 (s, 1H), 7.90 (s, 1H), 7.75 (m, 2H), 7.48-7.55 (m, 3H), 7.38 (m, 1H), 3.98 (s, 3H), 2.54 (s, 3H).

Example 22

[4-(5-Chloro-2-methyl-phenyl)-6-methyl-[1,3,5]triazin-2-yl]-(1H-indazol-6-yl)-amine A mixture of the title compound of Example 26 (200 mg, 0.54 mmol), methyl magnesium bromide (3 M in diethyl ether, 1.8 ml, 5.4 mmol), and tetrahydrofuran (4 ml) was stirred at 40° C. for 24 hours. After cooling in an ice bath, the reaction was quenched by dropwise addition of water (2 ml). The mixture was treated with hydrochloric acid (1 M, 25 ml), stirred for 5 minutes, and extracted with dichloromethane (50 ml). The organic extract was dried over sodium sulfate and concentrated under reduced pressure. The residue was purified by flash chromatography on silica gel eluting ethyl acetate-hexane (1:1) followed by recrystallization (ethyl acetate) to provide the title compound (40 mg, 21% yield). $^1$H NMR (DMSO-$d_6$) 12.95 (s, 1H) 10.41 (br s, 1H), 8.15 (s, 1H), 7.87-7.98 (m, 1H), 7.67-7.70 (m, 1H), 7.49-7.51 (m, 1H), 7.34-7.40 (m, 3H), 2.56 (s, 3H), 2.53 (s, 3H).

Example 23

(4-Bromo-phenyl)-[4-(5-chloro-2-methyl-phenyl)-6-methyl-[1,3,5]triazin-2-yl-amine The reaction of the title compound of Example 20 (200 mg, 0.49 mmol) with methyl magnesium bromide (3 M in diethyl ether, 1 ml, 3 mmol) in tetrahydrofuran (4 ml) using the method described in Example 22 provided the title compound (62 mg, 32% yield). $^1$H NMR (DMSO-$d_6$) 10.37 (s, 1H), 7.85 (s, 1H), 7.71 (m, 2H), 7.47-7.54 (m, 3H), 7.38 (m, 1H), 2.53 (s, 3H), 2.50 (s, 3H).

Example 24

(4-Bromo-phenyl)-[4-(5-chloro-2-methyl-phenyl)-6-ethyl-[1,3,5]triazin-2-yl-amine The reaction of the title compound of Example 20 (200 mg, 0.49 mmol) with ethyl magnesium bromide (1 M in diethyl ether, 7.5 ml, 7.5 mmol) in tetrahydrofuran (2 ml) using the method described in Example 22 provided the title compound (44 mg, 22% yield). $^1$H NMR (CDCl$_3$) 7.80 (m, 1H), 7.48 (d, J=8.8 Hz, 2H), 7.38 (d, J=8.8 Hz, 2H), 7.09-7.12 (m, 2H), 2.79 (q, J=7.4 Hz, 4H), 1.13 (t, J=7.0 Hz, 3H).

Example 25

6-(5-Chloro-2-methyl-phenyl)-N-(4-chloro-phenyl)-N-methyl-[1,3,5]triazine-2,4-diamine A mixture of 4-chloro-6-(5-chloro-2-methyl-phenyl)-[1,3,5]triazin-2-yl-amine (106 mg, 0.42 mmol), (4-chloro-phenyl)-methyl-amine (0.15 ml, 1.25 mmol), tetrahydrofuran (5 ml), and diisopropylethylamine (0.75 ml, 4.2 mmol) was heated at 40° C. for 72 hours. The mixture was concentrated under reduced pressure and the residue was dissolved in dichloromethane (25 ml). The solution was washed with hydrochloric acid (1 M, 25 ml) and concentrated under reduced pressure. The residue was purified by flash chromatography on silica gel eluting with 2% methanol-dichloromethane followed by 5% methanol-dichloromethane. Recrystallization (ethyl acetate-hexane) provided the title compound (33 mg, 22% yield). $^1$H NMR (DMSO-$d_6$) 7.78 (s, 1H), 7.37-7.46 (m, 4H), 7.26 (d, J=8.4 Hz, 1H), 7.10 (br s, 2H), 3.43 (s, 3H), 2.37 (s, 3H).

Example 26

[4-Chloro-6-(5-chloro-2-methyl-phenyl)-[1,3,5]triazin-2-yl]-(1H-indazol-6-yl)-amine A mixture of 2,4-dichloro-6-(5-chloro-2-methyl-phenyl)-[1,3,5]triazine (1 g, 3.6 mmol), 6-aminoindazole (0.5 g, 3.7 mmol), tetrahydrofuran (10 ml), and diisopropylethylamine (0.65 ml, 3.7 mmol) was stirred for 1 hour. After concentrating under reduced pressure, the residue was treated with water (25 ml) and stirred for 10 minutes. The solid was filtered, treated with hydrochloric acid (1 M, 10 ml), stirred vigorously for 10 minutes, and filtered. The solid was purified by flash chromatography on silica eluting with 5% methanol-dichloromethane to yield the title compound (600 mg, 45% yield). $^1$H NMR (DMSO-$d_6$) 13.04 (br s, 1H), 10.90-10.97 (m, 1H), 8.12 (s, 1H), 8.02 (s, 1H), 7.71 (m, 2H), 7.53 (m, 1H), 7.41 (m, 1H), 7.34 (m, 1H), 2.50-2.54 (m, 3H).

Example 27

[2-Aminimethyl-6-(5-chloro-2-methyl-phenyl)-[1,3,5]triazin-4-yl]-(4-bromo-phenyl)-amine To a suspension of lithium aluminum hydride (7 mg, 0.17 mmol) in anhydrous tetrahydrofuran (1.5 ml), cooled to −78° C., was added a solution of 6-(2,5-dichloro-2-methyl-phenyl)-(4-bromo-phenyl)-[1,3,5]-triazine-2-carbonitrile (35 mg, 0.09 mmol) in tetrahydrofuran (0.5 ml) dropwise during 10 minutes. After stirring at −78° C. for 2 hours, the reaction was quenched by dropwise addition of water (5 ml). The mixture was extracted with ethyl acetate (3×10 ml). The combined extracts were washed with water (25 ml), dried over sodium sulfate, and concentrated under reduced pressure. The residue was purified by preparative thin layer chromatography eluting with 7% methanol-dichloromethane to provide the title compound (16 mg, 48% yield) as a yellow powder. $^1$H NMR (CD$_3$OD) δ 7.85 (d, J=8.8 Hz, 2H), 7.31-7.75 (m, 5H), 3.60 (s, 2H).

Example 28

6-(5-Chloro-2-methyl-phenyl)-(4-bromo-phenyl)-[1,3,5]-triazine-2-carbonitrile

A solution of [6-(5-chloro-2-methyl-phenyl)-2-chloro-3-yl-[1,3,5]triazin-4-yl]-(4-bromo-phenyl)-amine (411 mg, 1.0 mmol), potassium cyanide (78 mg, 1.2 mmol), and anhydrous dimethylsulfoxide (20 ml) was heated at 60° C. for 4 hours. After cooling to room temperature, the solution was treated with water (50 ml) and extracted with dichloromethane (2×25 ml). The combined extracts were dried over sodium sulfate, and concentrating under reduced pressure. The residue was crystallized (ethyl acetate) to give the title compound (361 mg, 91% yield) as a yellow powder. $^1$H NMR (CD$_3$OD) δ 7.91 (d, J=8.9 Hz, 2H), 7.15-7.60 (m, 5H), 2.60 (s, 3H).

Example 29

(4-Bromo-phenyl)-[4-(5-chloro-2-methyl-phenyl)-6-methylsulfanyl-[1,3,5]triazin-2-yl]-amine A mixture of the title compound of Example 20 (234 mg, 0.57 mmol), sodium thiomethoxide (50 mg, 0.71 mmol), and tetrahydrofuran (5 ml) was stirred for 24 hours. After concentrating under reduced pressure, the residue was dissolved in dichloromethane (25 ml). The solution was washed with water (25 ml) and concentrated under reduced pressure. The residue was purified by flash chromatography on silica gel eluting with dichloromethane-hexane (1:1) to provide the title compound (137 mg, 57% yield). $^1$H NMR (DMSO-$d_6$) 10.42 (s, 1H), 7.88 (s, 1H), 7.70 (s, 2H), 7.45-7.55 (m, 3H), 7.38 (m, 1H), 2.55 (s, 3H), 2.50 (s, 3H).

Example 30

[6-(5-Chloro-2-methyl-phenyl)-2-chloro-3-yl-[1,3,5]-triazin-4-yl]-(4-nitro-phenyl)-amine A mixture of [6-(5-chloro-2-methyl-phenyl)-2,4-dichloro-1,3,5]-triazine (0.5 g, 1.82 mmol), 4-nitroaniline (277 mg, 2.0 mmol), anhydrous tetrahydrofuran (8 ml), and N,N-diisopropylethylamine (470 mg, 3.64 mmol) was stirred for 12 hours. The mixture was concentrated under reduced pressure and the residue was dissolved in dichloromethane (50 ml). The solution was washed with hydrochloric acid (1 M, 25 ml), washed with water (50 ml), dried over sodium sulfate, and concentrated under reduced pressure to provide the title compound (605 mg, 88% yield) as a yellow powder. $^1$H NMR (DMSO-$d_6$) δ 11.38 (br s, 1H), 8.31 (d, J=9.1 Hz, 2H), 7.99 (d, J=9.1 Hz, 2H), 7.92 (s, 1H), 7.38-7.56 (dd, J=2.3, 8.2 Hz, 1H), 7.42 (d, J=8.2 Hz, 1H), 2.51 (s, 3H).

Example 31

[6-(5-Chloro-2-methyl-phenyl)-2-piperidin-3-yl-[1,3,5]triazin-4-yl]-(4-chloro-phenyl)-amine A solution of [6-(5-chloro-2-methyl-phenyl)-2-chloro-3-yl-[1,3,5]triazin-4-yl]-(4-chloro-phenyl)-amine (150 mg, 0.41 mmol), piperidine (70 mg, 0.82 mmol), and ethylene glycol dimethyl ether (2 ml) was stirred at 80° C. for 16 hours. After concentrating under reduced pressure, the solid residue was recrystallized (ethyl acetate-hexane, 1:4) to provide the title compound (151 mg, 89% yield) as white flakes. $^1$H NMR (DMSO-$d_6$) δ 9.72 (br s, 1H), 7.85 (s, 1H), 7.75 (d, J=8.8 Hz, 2H), 7.47 (dd, J=2.4, 8.2 Hz, 1H), 7.40-7.34 (m, 3H), 3.82 (br s, 4H), 2.52 (s, 3H), 1.57-1.66 (m, 6H).

Example 32

6-(5-Chloro-2-methyl-phenyl)-N-(4-chloro-phenyl)-N,N-dimethy-[1,3,5]triazine-2,4-diamine A mixture of [6-(5-Chloro-2-methyl-phenyl)-2-chloro-3-yl-[1,3,5]triazin-4-yl]-(4-chloro-phenyl)-amine (150 mg, 0.41 mmol) and a saturated solution of dimethylamine in ethylene glycol dimethyl ether (2 ml) was stirred at 80° C. for 16 hours. After concentrating under reduced pressure, the solid residue was crystallized (ethyl acetate-hexane, 1:4) to provide the title compound (134 mg, 87% yield) as a white powder. $^1$H NMR (DMSO-$d_6$) δ 9.89 (br s, 1H), 7.87 (d, J=2.2 Hz, 1H), 7.81 (d, J=8.8 Hz, 2H), 7.47 (dd, J=2.4, 8.2 Hz, 1H), 7.36-7.39 (m, 3H), 3.25 (s, 6H), 2.52 (s, 3H).

Example 33

[6-(5-Chloro-2-methyl-phenyl)-[1,3,5]triazin-4-yl]-(4-chloro-phenyl)-amine

To a suspension of lithium aluminum hydride (31 mg, 0.82 mmol) in anhydrous tetrahydrofuran (2 ml), cooled to −78° C. was added a solution of [6-(5-Chloro-2-methyl-phenyl)-2-chloro-3-yl-[1,3,5]triazin-4-yl]-(4-chloro-phenyl)-amine (150 mg, 0.41 mmol) in tetrahydrofuran (1 ml) dropwise over 10 minutes. The mixture was stirred at −78° C. for 2 hours and at 0° C. for an additional 6 hours. The reaction was quenched by dropwise addition of water (5 ml) and extracted with ethyl acetate (2×15 ml). The combined extracts were washed with water (25 ml), dried over sodium sulfate, and concentrated under reduced pressure. The residue was purified by preparative thin layer chromatography eluting with hexane-dichloromethane (4:5) to provide the title compound (18 mg, 12% yield) as a white powder. $^1$H NMR (CD$_3$OD) δ 8.79 (s, 1H), 7.91 (s, 1H), 7.44 (br d, 2H), 7.18-7.38 (m, 4H), 2.52 (s, 3H).

Example 34

N-(4-Chloro-3-methylamino-phenyl)-6-(5-chloro-2-methyl-phenyl)-[1,3,5]triazine-2,4-diamine To a suspension of sodium hydride (60% in oil, 1.2 g, 30 mmol) in tetrahydrofuran (100 ml), cooled in an ice bath, was added slowly a solution of 2-chloro-5-nitroaniline (5 g, 29 mmol) in tetrahydrofuran (10 ml) followed by a solution of iodomethane (1.8 ml, 29 mmol) in tetrahydrofuran (10 ml). After stirring at room temperature for 20 hours, the mixture was concentrated under reduced pressure and the residue was partitioned between dichloromethane (100 ml) and water (100 ml). The organic layer was washed with saturated aqueous sodium chloride solution (50 ml), dried over sodium sulfate, and concentrated under reduced pressure. The residue was purified by flash chromatography on silica gel eluting with dichloromethane-hexane (1:3) and recrystalized (ethyl ether) to provide (2-chloro-5-nitro-phenyl)-methyl-amine (1.8 g, 33% yield) as orange crystals.

A solution of tin dichloride (4.0 g, 21.1 mmol) and (2-chloro-5-nitro-phenyl)-methyl-amine (1.0 g, 5.4 mmol) in concentrated hydrochloric acid (10 ml) was stirred for 2 hours. The mixture was treated with ethyl acetate (50 ml) and adjusted to pH 7 by slow addition of 1 M aqueous sodium hydroxide solution. The organic layer was dried over sodium sulfate and concentrated under reduced pressure to provide 4-chloro-N-3-methyl-benzene-1,3-diamine (800 mg, 95% yield).

The reaction of 2,4-dichloro-6-(5-chloro-2-methyl-phenyl)-[1,3,5]triazine and 4-chloro-N-3-methyl-benzene-1,3-diamine using the method described in Example 37 provided the title compound (28% yield). $^1$H NMR (DMSO-$d_6$) 9.47 (br s, 1H), 7.81 (s, 1H), 7.42 (d, 1H), 7.34 (d, J=8.2 Hz, 1H), 7.15-7.30 (m, 4H), 7.12 (d, J=8.4 Hz, 1H), 5.40 (m, 1H), 2.78 (s, 3H), 2.55 (s, 3H).

Example 35

[6-(5-Chloro-2-methyl-phenyl)-2-chloro-3-yl-[1,3,5]-triazin-4-yl]-(4-azido-phenyl)-amine A mixture of [6-(5-chloro-2-methyl-phenyl)-2,4-dichloro-[1,3,5]-triazine] (242 mg, 0.88 mmol), 4-azidoaniline hydrochloride (150 mg, 0.88 mmol), anhydrous tetrahydrofuran (8 ml), and N,N-diisopropylethylamine (227 mg, 1.76 mmol) was stirred for 3 hours. After concentrating under reduced pressure, the residue was purified by flash chromatography on silica gel eluting with dichloromethane-hexane (1:1) to provide the title compound (279 mg, 85% yield) as a yellow powder. $^1$H NMR (DMSO-$d_6$) δ 10.89 (br s, 1H), 7.95 (br d, 1H), 7.68-7.74 (m, 2H), 7.38-7.56 (m, 2H), 7.15-7.20 (m, 2H), 2.52 (s, 3H).

Example 36

6-(5-Chloro-2-methyl-phenyl)-N-(4-azido-phenyl)-amino-[1,3,5]triazine-2,4-diamine To a saturated solution of ammonia in tetrahydrofuran (4 ml) was added [6-(5-chloro-2-methyl-phenyl)-2-chloro-3-yl-[1,3,5]-triazin-4-yl]-(4-azido-phenyl)-amine (56 mg, 0.15 mmol). After stirring for 16 hours, the mixture was concentrated under reduced pressure. The residue was purified by preparative thin layer chromatography eluting with methanol-dichloromethane-hexane (1:25:25) to provide the title compound (45 mg, 85% yield) as a white powder. $^1$H NMR (DMSO-$d_6$) δ 9.71 (br s, 1H), 7.82 (br s, 2H), 7.75 (d, J=2.3 Hz, 1H), 7.41 (dd, J=2.4, 8.2 Hz, 1H ), 7.31 (d, J=8.2 Hz, 1H), 7.23 (br s, 2H), 7.04 (d, J=8.8 Hz, 2H), 2.52 (s, 3H).

Example 37

6-(5-Chloro-2-methyl-phenyl)-N-indan-5-yl-[1,3,5]triazine-2,4-diamine

A mixture of 2,4-dichloro-6-(5-chloro-2-methyl-phenyl)-[1,3,5]triazine (550 mg, 2 mmol), 4-aminoindane (133 mg, 2 mmol), tetrahydrofuran (10 ml), and N,N-diisopropylethylamine (0.52 ml, 3.0 mmol) was stirred for 18 hours. After diluting with tetrahydrofuran (10 ml), the mixture was washed with a solution composed of saturated aqueous sodium chloride solution (10 ml) and 1 M hydrochloric acid (10 ml). The organic layer was treated with a solution of ammonia in methanol (7 M, 7 ml). After stirring for 16 hours, the mixture was concentrated under reduced pressure. The residue was dissolved in tetrahydrofuran (15 ml), washed with saturated aqueous sodium chloride solution (15 ml), and concentrated under reduced pressure. The residue was purified by flash chromatography on silica gel eluting with ethyl acetate-hexane (1:3) to provide the title compound (120 mg, 34% yield for 2 steps). $^1$H NMR (DMSO-$d_6$) 9.44 (br s, 1H), 7.77 (s, 1H), 7.64 (s, 1H), 7.42 (br s, 1H), 7.40 (d, J=7.5 Hz, 1H), 7.32 (d, J=7.5 Hz, 1H), 7.14 (m, 3H), 2.85 (m, 4H), 2.52 (s, 3H), 2.04 (m, 2H).

Example 38

6-(5-Chloro-2-methyl-phenyl)-N-(4-ethyl-phenyl)-[1,3,5]triazine-2,4-diamine

The reaction of 2,4-dichloro-6-(5-chloro-2-methyl-phenyl)-[1,3,5]triazine and 4-ethylaniline using the method described in Example 37 provided the title compound (58% yield). $^1$H NMR (DMSO-$d_6$) 9.49 (br s, 1H), 7.77 (d, J=2.3 Hz, 1H), 7.66 (br s, 2H), 7.43 (dd, J=8.2 Hz and 2.4 Hz, 1H), 7.33 (d, J=8.2 Hz, 1H) 7.12-7.18 (m, 4H), 2.53-2.59 (m, 5H), 1.19 (t, J=7.6 Hz, 3H).

Example 39

6-(5-Chloro-2-methyl-phenyl)-N—P-tolyl-[1,3,5]triazine-2,4-diamine

The reaction of 2,4-dichloro-6-(5-chloro-2-methyl-phenyl)-[1,3,5]triazine and p-toluidine using the method described in Example 37 provided the title compound (47% yield). $^1$H NMR (DMSO-$d_6$) 9.49 (br s, 1H), 7.77 (d, J=2.4 Hz, 1H), 7.66 (br s, 2H), 7.44 (dd, J=8.2 Hz and 2.4 Hz, 1H), 7.33 (d, J=8.2 Hz, 1H), 7.09-7.18 (m, 4H), 2.52 (s, 3H), 1.51 (s, 3H).

Example 40

N-(4-Bromophenyl)-6-(5-chloro-2-trifluoromethylphenyl)-[1,3,5]triazine-2,4-diamine To a mixture of 5-chloro-2-trifluoromethylbenzoic acid (2.25 g, 10.0 mmol) and dichloromethane (40 ml) was added oxalyl chloride (1.1 ml, 12.6 mmol) followed by N,N-dimethylformamide (5 drops). After stirring for 90 minutes, methanol (5 ml) was added. After stirring for 30 minutes, the mixture was concentrated under reduced pressure. The residue was dissolved in ethyl acetate (50 ml). The solution was washed with water (50 ml), washed with aqueous sodium carbonate solution (0.5 M, 2×50 ml), dried over sodium sulfate, and concentrated under reduced pressure to provide 5-chloro-2-trifluoromethylbenzoate (2.14 g, 90% yield).

The reaction of 1-(4-bromophenyl)biguanidine hydrochloride with methyl 5-chloro-2-trifluoromethylbenzoate using the method described in Example 2 provided the title compound (40% yield). $^1$H NMR (DMSO-$d_6$) δ 9.82 (br s, 1H), 7.75-7.88 (m, 5H), 7.36-7.44 (m, 4H).

Example 41

{4-[4-Chloro-6-(5-chloro-2-methyl-phenyl)-[1,3,5]triazin-2-ylamino]-phenyl}-methanol The reaction of 2,4-dichloro-6-(5-chloro-2-methyl-phenyl)-[1,3,5]triazine and 4-aminobenzyl alcohol using the method described in Example 37 provided the title compound (50 mg, 62% yield). $^1$H NMR (DMSO-$d_6$) 9.52 (br s, 1H), 7.77 (s, 1H), 7.70 (s, 2H), 7.42 (d, 1H), 7.33 (d, 1H), 7.24 (m, 4H), 5.07 (m, 1H), 4.45 (d, J=5.7 Hz, 2H), 2.52 (s, 3H).

Example 42

6-(5-Chloro-2-methyl-phenyl)-N-(4-ethynyl-phenyl)-[1,3,5]triazine-2,4-diamine

The reaction of 2,4-dichloro-6-(5-chloro-2-methyl-phenyl)-[1,3,5]triazine and 4-ethynylaniline using the method described in Example 37 provided the title compound (457 mg, 46% yield). $^1$H NMR (DMSO-$d_6$) 9.82 (s, 1H), 7.87 (d, J=8.1 Hz, 2H), 7.78 (d, J=2.4 Hz, 1H), 7.32-7.45 (m, 6H), 4.07 (s, 1H), 2.53 (s, 3H).

Example 43

5-[4-Amino-6-(5-chloro-2-methylphenyl)-[1,3,5]triazin-2-ylamino]-2-chloro-N-methylbenzamide To a mixture of 2-chloro-5-nitrobenzoic acid (5.0 g, 25.0 mmol) and dichloromethane (100 ml) was added oxalyl chloride (2.7 ml, 31.0 mmol) followed by N,N-dimethylformamide (5 drops). After stirring for 2 hours, the mixture was concentrated under reduced pressure to provide 2-chloro-5-nitro-benzoyl chloride.

A mixture of 2-chloro-5-nitro-benzoyl chloride (502 mg, 2.3 mmol), methylamine hydrochloride (213 mg, 3.1 mmol), dichloromethane (10 ml), and triethylamine (0.84 ml, 6.0 mmol) was stirred for 60 hours. The mixture was treated with ethyl acetate (25 ml). The solution was washed with a mixture of saturated aqueous sodium chloride solution and 1 M hydrochloric acid (1:1, 2×20 ml), washed with aqueous sodium carbonate solution (1 M, 20 ml), dried over sodium sulfate, and concentrated under reduced pressure to provide 2-chloro-N-methyl-5-nitro-benzamide.

To a suspension of 2-chloro-N-methyl-5-nitro-benzamide (2.3 mmol) in concentrated hydrochloric acid (3 ml) was added a solution of tin dichloride (1.4 g, 7.2 mmol) in concentrated hydrochloric acid (4 ml). After stirring for 20 hours, the mixture was cooled in an ice bath and treated with 50% sodium hydroxide to basic pH. The mixture was extracted with ethyl acetate (3×25 ml). The combined extracts were dried over sodium sulfate and concentrated under reduced pressure to provide 5-amino-2-chloro-N-methylbenzamide (274 mg, 88% yield).

The reaction of 2,4-dichloro-6-(5-chloro-2-methyl-phenyl)-[1,3,5]triazine and 5-amino-2-chloro-N-methylbenzamide using the method described in Example 37 provided the title compound (222 mg, 55% yield). $^1$H NMR (DMSO-$d_6$) δ 9.80 (br s, 1H), 8.32 (q, 1H, J=4 Hz), 7.86 (br s, 2H), 7.78 (d, 1H, J=2 Hz), 7.31-7.44 (m, 5H), 2.75 (d, 3H, J=4 Hz), 2.52 (s, 3H).

Example 44

6-(5-Chloro-2-methylaminophenyl)-N-(4-chlorophenyl)-[1,3,5]triazine-2,4-diamine

A mixture of methyl 2-amino-5-chlorobenzoate (1.0 g, 5.4 mmol), iodomethane (0.75 ml, 12.0 mmol), potassium carbonate (1.7 g, 12.4 mmol), and acetonitrile (20 ml) was stirred for 48 hours. The mixture was filtered through a pad of celite under suction and the filtrate was concentrated under reduced pressure. The residue was purified by flash chromatography on silica eluting with ethyl acetate-hexane (1:19) to provide 5-chloro-2-methylaminobenzoic acid methyl ester (137 mg, 13% yield) followed by 5-chloro-2-dimethylaminobenzoic acid methyl ester (809 mg, 70% yield).

The reaction of 1-(4-chlorophenyl)biguanidine hydrochloride with methyl 5-chloro-2-methylaminobenzoate using the method described in Example 2 provided the title compound (179 mg, 25% yield). $^1$H NMR (DMSO-$d_6$) δ 9.69 (br s, 1H), 9.18 (q, 1H, J=5 Hz), 8.35 (d, 1H, J=2 Hz), 7.79 (br s, 1H), 7.22-7.37 (m, 5H), 6.69 (d, 1H, J=9 Hz), 2.86 (d, 3H, J=5 Hz).

Example 45

6-(5-Bromo-2-chloro-phenyl)-N-(4-chloro-phenyl)-[1,3,5]triazine-2,4-diamine

To a suspension of 5-bromo-2-chloro-benzoic acid (2.5 g, 10.6 mmol) in dichloromethane (50 ml) was added a solution of oxalyl chloride in dichloromethane (2 M, 6 ml, 12 mmol) followed by N,N-dimethylformamide (5 drops). After stirring for 30 minutes, methanol (10 ml) was added and the mixture was stirred for 20 hours. The mixture was concentrated under reduced pressure and partitioned between ethyl acetate (150 ml) and saturated aqueous potassium carbonate solution (100 ml). The organic layer was concentrated under reduced pressure to provide methyl 5-bromo-2-chloro-benzoate (2.4 g, 91% yield).

The reaction of 1-(4-chlorophenyl)biguanidine hydrochloride and methyl 5-bromo-2-chloro-benzoate using the method described in Example 2 provided the title compound (418 mg, 51% yield). $^1$H NMR (DMSO-$d_6$) 9.85 (br s, 1H), 7.84 (m, 3H), 7.69 (m, 1H), 7.52 (d, J=8.6 Hz, 1H), 7.40 (s, 2H), 7.33 (d, J=8.9 Hz, 2H).

Example 46

{4-[4-Amino-6-(2,5-dichloro-phenyl)-[1,3,5]triazin-2-ylamino]-phenyl}-methanol

The reaction of 2,4-dichloro-6-(2,5-dichloro-phenyl)-[1,3,5]triazine and 4-aminobenzyl alcohol using the method described in Example 37 provided the title compound (560 mg, 77% yield). $^1$H NMR (DMSO-$d_6$) 9.65 (br s, 1H), 7.74 (m, 3H), 7.60 (m, 2H), 7.26 (br s, 2H), 7.24 (d, J=8.4 Hz, 2H), 5.05 (br s, 1H), 4.40 (s, 2H).

Example 47

6-(5-Chloro-2-dimethylaminophenyl)-N-(4-chlorophenyl)-[1,3,5]triazine-2,4-diamine A mixture of methyl 2-amino-5-chlorobenzoate (1.0 g, 5.4 mmol), iodomethane (0.75 ml, 12.0 mmol), potassium carbonate (1.7 g, 12.4 mmol), and acetonitrile (20 ml) was stirred for 48 hours. The mixture was filtered through a pad of celite under suction and the filtrate was concentrated under reduced pressure. The residue was purified by flash chromatography on silica eluting with ethyl acetate-hexane (1:19) to provide 5-chloro-2-methylaminobenzoic acid methyl ester (137 mg, 13% yield) followed by 5-chloro-2-dimethylaminobenzoic acid methyl ester (809 mg, 70% yield).

The reaction of 1-(4-chlorophenyl)biguanidine hydrochloride with methyl 5-chloro-2-dimethylaminobenzoate using the method described in Example 2 provided the title compound (110 mg, 20% yield). $^1$H NMR (DMSO-$d_6$) δ 9.72 (br s, 1H), 7.87 (d, 2H, J=9 Hz), 7.42 (br s, 1H), 7.15-7.33 (m, 5H), 6.96 (d, 1H, J=9 Hz), 2.70 (s, 6H).

Example 48

6-(2,5-Dichloro-phenyl)-N-(1H-indazol-6-yl)-[1,3,5]triazine-2,4-diamine

The reaction of 2,4-dichloro-6-(2,5-dichloro-phenyl)-[1,3,5]triazine and 6-aminoindazole using the method described in Example 37 provided the title compound (148 mg, 40% yield). $^1$H NMR (DMSO-$d_6$) 12.85 (s, 1H) 9.83 (br s, 1H), 8.05 (s, 1H), 7.94 (s, 1H), 7.28 (s, 1H), 7.55-7.63 (m, 4H), 7.50 (s, 1H), 7.35 (s, 1H).

Example 49

6-(2,5-Dichloro-phenyl)-N—P-tolyl-[1,3,5]triazine-2,4-diamine

The reaction of 1-(4-methyl-phenyl)biguanidine hydrochloride with methyl 2,5-dichlorobenzoate using the method described in Example 2 provided the title compound (53 mg, 17% yield). $^1$H NMR (DMSO-$d_6$) 9.62 (br s, 1H), 7.66-7.70 (m, 3H), 7.54-7.60 (m, 2H), 7.30 (br s, 2H), 7.10 (d, J=8.3 Hz, 2H), 2.26 (s, 3H).

Example 50

N-(4-Chloro-phenyl)-6-(5-chloro-2-propoxy-phenyl)-[1,3,5]triazine-2,4-diamine

A mixture of 1-bromo-propane (1 ml, 11 mmol), methyl 5-chloro-2-hydroxy-benzoate (1.0 g, 5.4 mmol), potassium carbonate (1.5 g, 10.9 mmol), and acetonitrile (20 ml) was heated under reflux for 4 hours. After cooling to room temperature, the mixture was filtered and the filtrate was concentrated under reduced pressure. The residue was partitioned between ethyl acetate (100 ml) and saturated aqueous sodium chloride solution (50 ml). The organic layer was concentrated under reduced pressure to provide methyl 5-chloro-2-propoxy-benzoate (1.2 g, 97% yield).

The reaction of 1-(4-chlorophenyl)biguanidine hydrochloride and methyl 5-chloro-2-propoxy-benzoate using the method described in Example 2 provided the title compound (270 mg, 35% yield). $^1$H NMR (DMSO-$d_6$) 9.68 (br s, 1H), 7.87 (d, J=8.8 Hz, 2H), 7.46 (s, 1H), 7.41 (d, J=8.6 Hz, 1H), 7.31 (d, J=8.8 Hz, 2H), 7.18 (br s, 2H), 7.14 (d, J=8.8 Hz, 1H).

Example 51

6-(5-Chloro-2-ethoxy-phenyl)-N-(1H-indazol-6-yl)-[1,3,5]triazine-2,4-diamine

The reaction of 2,4-dichloro-6-(5-chloro-2-ethoxy-phenyl)-[1,3,5]triazine and 6-aminoindazole using the method described in Example 37 provided the title compound (114 mg, 30% yield). $^1$H NMR (DMSO-$d_6$) 12.82 (s, 1H), 9.71 (br s, 1H), 8.12 (s, 1H), 7.93 (s, 1H), 7.62 (d, J=8.7 Hz, 1H), 7.52 (s, 1H), 7.47 (m, 2H), 7.16 (m, 3H), 4.13 (m, 2H), 1.26 (m, 3H).

Example 52

6-(5-Chloro-2-isopropoxy-phenyl)-N-(4-chloro-phenyl)-[1,3,5]triazine-2,4-diamine A mixture of 2-iodo-propane (2.2 ml, 22 mmol), methyl 5-chloro-2-hydroxy-benzoate (2.0 g, 10.7 mmol), potassium carbonate (3.0 g, 10.9 mmol), and acetonitrile (40 ml) was heated under reflux for 3 hours. After cooling to room temperature, the mixture was filtered and the filtrate was concentrated under reduced pressure. The residue was partitioned between ethyl acetate (100 ml) and saturated aqueous sodium chloride solution (100 ml). The organic layer was dried over sodium sulfate and concentrated under reduced pressure. The residue was purified by flash chromatography on silica gel eluting with dichloromethane-hexane (1:3 followed by 1:2 followed by 1:1) to provide methyl 5-chloro-2-isopropoxy-benzoate (1.2 g, 49% yield).

The reaction of 1-(4-chlorophenyl)biguanidine hydrochloride and methyl 5-chloro-2-isopropoxy-benzoate using the method described in Example 2 provided the title compound (230 mg, 29% yield). $^1$H NMR (DMSO-$d_6$) 9.68 (br s, 1H), 7.88 (d, J=8.9 Hz, 2H), 7.45 (s, 1H), 7.40 (m, 1H), 7.30 (d, J=8.8 Hz, 2H), 7.18 (s, 2H), 7.15 (d, J=8.9 Hz, 2H), 4.52 (m, 1H), 1.22 (m, 6H).

Example 53

{4-[4-Amino-6-(5-chloro-2-ethoxy-phenyl)[1,3,5]triazin-2-ylamino]-phenyl}-methanol The reaction of 2,4-dichloro-6-(5-chloro-2-ethoxy-phenyl)-[1,3,5]triazine and 4-aminobenzyl alcohol using the method described in Example 37 provided the title compound (230 mg, 31% yield). $^1$H NMR (DMSO-$d_6$) 9.55 (br s, 1H), 7.78 (d, J=8.1 Hz, 2H), 7.51 (s, 1H), 7.46 (d, J=8.8 Hz, 1H), 7.22 (d, J=8.0, 2H), 7.15 (m, 3H), 5.06 (m, 1H), 4.44 (s, 2H), 4.10 (m, 2H), 3.61 (br s, 1H), 1.31 (m, 3H).

Example 54

6-(5-Chloro-2-ethoxyphenyl)-N-(4-nitrophenyl)-[1,3,5]triazine-2,4-diamine

The reaction of 2,4-dichloro-6-(5-chloro-2-ethoxyphenyl)-[1,3,5]triazine and 4-nitroaniline using the method described in Example 37 provided the title compound (586 mg, 73% yield). $^1$H NMR (DMSO-$d_6$) δ 10.35 (br s, 1H), 8.12-8.19 (m, 4H), 7.36-7.57 (m, 4H), 7.17 (d, 1H, J=9 Hz), 4.12 (q, 2H, J=7 Hz), 1.29 (t, 3H, J=7 Hz).

Example 55

N-Benzo[1.3]dioxol-5-yl-6-(5-chloro-2-ethoxy-phenyl)[1,3,5]triazine-2,4-diamine

The reaction of 2,4-dichloro-6-(5-chloro-2-ethoxy-phenyl)-[1,3,5]triazine and 3,4-(methylenedioxy)-aniline using the method described in Example 37 provided the title compound (30 mg, 4% yield). $^1$H NMR (DMSO-$d_6$) 9.50 (br s, 1H), 7.67 (s, 1H), 7.50 (s, 1H), 7.45 (d, J=8.8 Hz, 1H), 7.14 (d, J=8.8, 2H), 7.10 (m, 3H), 6.82 (d, J=8.4 Hz, 1H), 5.96 (s, 2H), 4.08 (m, 2H), 1.30 (m, 3H).

Example 56

6-(5-Chloro-2-ethoxyphenyl)-N-(4-nitrophenyl)-[1,3,5]triazine-2,4-diamine

The reaction of 2,4-dichloro-6-(5-chloro-2-ethoxyphenyl)-[1,3,5]triazine and 4-bromoaniline using the method described in Example 37 provided the title compound (261 mg, 53% yield). $^1$H NMR (DMSO-$d_6$) δ 9.75 (br s, 1H), 7.83 (d, 2H, J=9 Hz), 7.43-7.52 (m, 4H), 7.13-7.20 (m, 3H), 4.09 (q, 3H, J=7 Hz), 1.28 (t, 3H, J=7 Hz).

Example 57

2-{4-[4-Amino-6-(5-chloro-2-methyl-phenyl)-[1,3,5]triazin-2-ylamino]-phenyl}-ethanol The reaction of 2,4-dichloro-6-(5-chloro-2-methyl-phenyl)-[1,3,5]triazine and 4-aminophenethyl alcohol using the method described in Example 37 provided the title compound (150 mg, 42% yield). $^1$H NMR (DMSO-$d_6$) 9.48 (br s, 1H), 7.76 (s, 1H), 7.64 (s, 2H), 7.43 (m, 1H), 7.32 (m, 1H), 7.16 (s, 2H), 7.13 (d, J=8.2 Hz, 2H), 4.61 (s, 1H), 3.58 (t, J=7.1 Hz, 2H), 2.69 (t, J=6.9 Hz, 2H), 2.52 (s, 3H).

Example 58

6-(5-Chloro-2-methyl-phenyl)-N-(4-dimethylaminomethyl-phenyl)-[1,3,5]triazine-2,4-diamine A mixture of 4-nitrobenzyl bromide (2.16 g, 10 mmol), a solution of dimethylamine in methanol (2 M, 50 ml, 100 mmol), N,N-dimethylformamide (20 ml), and potassium carbonate (2.07 g, 15 mmol) was stirred for 12 hours. The methanol was removed by concentrating under reduced pressure and the mixture was treated with ethyl acetate (200 ml). The mixture was washed with water (100 ml), dried over anhydrous magnesium sulfate, and concentrated under reduced pressure to yield 4-(N,N-dimethylaminomethyl)-4-nitrobenzene (0.98 g, 72% yield).

A mixture of 4-(N,N-dimethylaminomethyl)-4-nitrobenzene (0.98 g, 5.8 mmol), ethyl acetate (50 ml), and 10% palladium on carbon (200 mg) was treated with hydrogen gas (40 psi) on a Parr shaker for 1 hour. The mixture was filtered through a pad of celite under suction and the filtrate was concentrated under reduced pressure to yield 4-(N,N-dimethylaminomethyl)-aniline (0.77 g, 97% yield).

A solution of 2,4-dichloro-6-(5-chloro-2-methyl-phenyl)-[1,3,5]triazine (275 mg, 1 mmol), 4-N,N-dimethylaminomethylaniline (150 mg, 1 mmol), tetrahydrofuran (10 ml), and N,N-diisopropylethylamine (129 mg, 1 mmol) was stirred for 4 hours. After concentrating under reduced pressure, the residue was dissolved in ethyl acetate (15 ml). The solution was washed with cold hydrochloric acid (1 M, 10 ml), washed with water (10 ml), dried over anhydrous magnesium sulfate, and concentrated under reduced pressure. The residue was purified by flash chromatography on silica gel eluting with 5% methanol-ethyl acetate to provide [4-chloro-6-(5-chloro-2-methyl-phenyl)-[1,3,5]-triazin-2-yl]-(4-dimethylaminomethyl-phenyl)-amine (0.305 g, 78% yield). $^1$H NMR (CDCl$_3$) δ 8.0 (s, 1H), 7-7.8 (m, 6H), 3.3 (d, 6H) 2.6 (s, 3H).

A pressure bottle was charged with [4-chloro-6-(5-chloro-2-methyl-phenyl)-[1,3,5]-triazin-2-yl]-(4-dimethylaminomethyl-phenyl)-amine (0.305 g, 0.79 mmol) and tetrahydrofuran (20 ml) and cooled to −78° C. A slow stream of ammonia gas was passed into the solution for 2 minutes and the bottle was sealed. After stirring at room temperature for 12 hours, the mixture was concentrated under reduced pressure. The residue was purified by flash chromatography on silica gel eluting with 10% methanol-ethyl acetate to provide the title compound (0.148 g, 49% yield). $^1$H NMR (CDCl$_3$) δ 7.9 (s, 1H), 7.2-7.6 (m, 6H), 3.25 (d, 6H) 2.5 (s, 3H).

Example 59

6-(5-Chloro-2-methyl-phenyl)-N-(3,4-dimethyl-phenyl)-[1,3,5]triazine-2,4-diamine The reaction of 2,4-dichloro-6-(5-chloro-2-methyl-phenyl)-[1,3,5]triazine and 3,4-dimethylaniline using the method described in Example 37 provided the title compound (215 mg, 63% yield). $^1$H NMR (DMSO-$d_6$) 9.39 (br s, 1H), 7.79 (s, 1H), 7.54 (s, 1H), 7.48 (br s, 2H), 7.43 (m, 1H), 7.33 (m, 1H), 7.15 (br s, 2H), 7.05 (m, 1H), 2.54 (s, 3H), 2.21 (s, 3H), 2.17 (s, 3H).

Example 60

{4-[4-Amino-6-(5-chloro-2-methyl-phenyl)-[1,3,5]triazin-2-ylamino]-phenyl}-acetic acid The reaction of 2,4-dichloro-6-(5-chloro-2-methyl-phenyl)-[1,3,5]triazine and 4-aminophenylacetic acid using the method described in Example 37 provided the title compound (265 mg, 72% yield). $^1$H NMR (DMSO-$d_6$) 12.21 (br s, 1H) 9.53 (br s, 1H), 7.76 (m, 1H), 7.70 (m, 2H), 7.43 (m, 1H), 7.32 (m, 1H), 7.17 (m, 4H), 3.50 (s, 2H), 2.52 (s, 3H).

Example 61

6-(5-Chloro-2-ethoxyphenyl)-N—P-tolyl-[1,3,5]triazine-2,4-diamine

The reaction of 2,4-dichloro-6-(5-chloro-2-ethoxy-phenyl)-[1,3,5]triazine and p-toluidine using the method described in Example 37 provided the title compound (73 mg, 20% yield). $^1$H NMR (DMSO-$d_6$) 9.50 (br s, 1H), 7.71 (d, J=8.4 Hz, 2H), 7.43-7.50 (m, 2H), 7.15 (dd, J=24.0, 8.6 Hz, 5H), 4.11 (q, J=6.8 Hz, 2H), 2.25 (s, 3H), 1.30 (t, J=6.9 Hz, 3H).

Example 62

5-[4-Amino-6-(5-chloro-2-ethoxyphenyl)-[1,3,5]triazin-2-ylamino]-2-chloro-N-methylbenzamide 5-Amino-2-chloro-N-methylbenzamide was synthesized by the method described in Example 43.

The reaction of 2,4-dichloro-6-(5-chloro-2-ethoxyphenyl)-[1,3,5]triazine and 5-amino-2-chloro-N-methylbenzamide using the method described in Example 37 provided the title compound (147 mg, 35% yield). $^1$H NMR (DMSO-$d_6$) δ 9.78 (br s, 1H), 8.30 (q, 1H, J=5 Hz), 7.85-7.99 (m, 2H), 7.14-7.52 (m, 6H), 4.08 (q, 2H, J=7 Hz), 2.77 (d, 3H, J=8 Hz), 1.27 (t, 3H, J=7 Hz).

Example 63

(S)-2-Amino-pentanedioic acid 5-{4-[4-amino-6-(5-chloro-2-methyl-phenyl)-[1,3,5]triazin-2-ylamino]-benzyl}ester A mixture of the title compound of Example 41 (1.0 g, 2.92 mmol), N-butoxycarbonyl glutamic acid α-tert-butyl ester (0.975 g, 3.22 mmol), N,N-dimethylaminopyridine (0.071 g, 0.58 mmol), N,N-dimethylformamide (10 ml), and N,N-diisopropylcarbodiimide (0.479 g, 3.8 mmol) was stirred for 12 hours. The mixture was treated with water (100 ml) and extracted with ethyl acetate (4×50 ml). The combined extracts were washed with water (2×50 ml), dried over magnesium sulfate, and concentrated under reduced pressure. The residue was purified by flash chromatography eluting with 30% ethyl acetate-hexane to provide 2-tert-butoxycarbonylamino-pentanedioic acid 5-{4-[4-amino-6-(5-chloro-2-methyl-phenyl)-[1,3,5]triazin-2-ylamino]-benzyl}ester 1-tert-butyl ester (1.45 g, 79% yield). $^1$H NMR (CDCl$_3$) δ 7.78 (s, 1H), 7.58-7.60 (br s, 2H), 7.30-7.34 (m, 4H), 7.19-7.21 (d, 1H), 5.3-5.5 (br s, 2H), 5.10-5.2 (br s, 1H) 5.10 (s, 2H) 4.2-4.3 (m, 1H) 2.55 (s, 3H) 2.3-2.5 (m, 2H), 2.1-2.25 (m, 1H) 1.85-2 (m, 1H) 1.45 (s, 9H) 1.40 (s, 9H).

A mixture of 2-tert-butoxycarbonylamino-pentanedioic acid 5-{4-[4-amino-6-(5-chloro-2-methyl-phenyl)-[1,3,5]triazin-2-ylamino]-benzyl}ester 1-tert-butyl ester (1.45 g, 2.3 mmol), acetic acid (10 ml), dichloromethane (5 ml), and a solution of hydrogen chloride in 1,4-dioxane (4 M, 10 ml) was stirred for 12 hours. The mixture was poured into ethyl acetate (50 ml). The solid was filtered and dried under reduced pressure to provide the hydrochloride salt of the title compound (0.98 g, 75% yield). $^1$H NMR (CD$_3$OD) δ 7.78 (s, 1H), 7.7-7.9 (br s, 2H), 7.58 (d, 2H), 7.46 (d, 4H), 5.18 (s, 2H) 4.09 (t, 1H) 2.58-2.82 (m, 2H) 2.58 (br s, 3H), 2.1-2.3 (m, 2H).

Example 64

(S)-2-Amino-pentanedioic acid 1-{4-[4-amino-6-(5-chloro-2-methyl-phenyl)-[1,3,5]-triazin-2-ylamino]-benzyl}ester The title compound was synthesized according to the method described in Example 63 using the title compound of Example 41 and N-tert-butoxycarbonyl glutamic acid γ-tert-butyl ester (74% yield). $^1$H NMR (CD$_3$OD) δ 7.75-8 (br s, 2H), 7.75 (s, 1H), 7.59 (d, 2H), 7.5 (d, 4H), 7.45 (d, 2H), 5.32 (s, 2H) 4.11 (t, 1H) 2.55 (s, 3H) 2.45-2.56 (m, 2H), 2.1-2.25 (m, 2H).

Example 65

6-[5-Chloro-2-(2-methoxy-ethoxy)-phenyl]-N-(4-chloro-phenyl)[1,3,5]triazine-2,4-diamine A mixture of 5-chlorosalicylic acid (5.0 g, 29.0 mmol), potassium carbonate (10.8 g, 78.1 mmol), acetonitrile (100 ml), and 2-bromoethylmethyl ether (6.8 ml, 72.3 mmol) was heated under reflux for 20 hours. The mixture was filtered and the filtrate was concentrated under reduced pressure. The residue was dissolved in ethyl acetate (50 ml). The solution was washed with aqueous sodium hydroxide solution (1 M, 2×50 ml), washed with water (50 ml), dried over sodium sulfate, and concentrated under reduced pressure to provide 5-chloro-2-(2-methoxyethoxy)benzoic acid 2-methoxyethyl ester (7.83 g, 93% yield).

The reaction of 1-(4-chlorophenyl)biguanidine hydrochloride and methoxyethyl 5-chloro-2-(2-methoxy-ethoxy)-benzoate using the method described in Example 2 provided the title compound (530 mg, 65% yield). $^1$H NMR (DMSO-d$_6$) 9.70 (br s, 1H), 7.87 (d, J=8.9 Hz, 2H), 7.50 (s, 1H), 7.45 (m, 1H), 7.32 (d, J=8.9 Hz, 2H), 7.20 (s, 2H), 7.17 (d, J=8.9 Hz, 2H), 4.15 (m, 2H), 3.61 (m, 2H), 3.22 (m, 3H).

Example 66

6-(5-Chloro-2-methyl-phenyl)-N-(3-ethyl-phenyl)-[1,3,5]triazine-2,4-diamine

The reaction of 2,4-dichloro-6-(5-chloro-2-methyl-phenyl)-[1,3,5]triazine and 3-ethylaniline using the method described in Example 37 provided the title compound (80 mg, 24% yield). $^1$H NMR (DMSO-d$_6$) 9.48 (br s, 1H), 7.79 (s, 1H), 7.63 (s, 2H), 7.42 (d, J=8.2 Hz, 1H), 7.33 (d, J=8.2 Hz, 1H), 7.20 (m, 3H), 6.85 (d, J=7.4 Hz, 2H), 2.61 (q, J=7.5 Hz, 2H), 2.53 (s, 3H), 1.21 (t, J=7.6 Hz, 3H).

Example 67

6-(5-Chloro-2-methyl-phenyl)-N-(4-vinyl-phenyl)-[1,3,5]triazine-2,4-diamine

A mixture of 2,4-dichloro-6-(5-chloro-2-methyl-phenyl)-[1,3,5]triazine (500 mg, 1.8 mmol), 4-vinylphenylamine (228 mg, 1.9 mmol), tetrahydrofuran (20 ml), and N,N-diisopropylethylamine (0.63 ml, 3.6 mmol) was stirred for 2 hours. The mixture was transferred to a pressure bottle and chilled to −78° C. A slow stream of ammonia gas was passed into the mixture for 2 minutes and the bottle was sealed. After stirring at room temperature for 60 hours, the mixture was concentrated under reduced pressure. The residue was purified by flash chromatography on silica gel eluting with ethyl acetate-hexane (1:3) to provide the title compound (260 mg, 41% yield). $^1$H NMR (acetone-d$_6$) 8.78 (br s, 1H), 7.92 (d, J=2.4 Hz, 1H), 7.88 (d, J=8.3 Hz, 2H), 7.44 (d, J=8.6 Hz, 2H), 7.39 (dd, J=2.4 Hz, J=8.2 Hz, 1H), 7.30 (d, J=8.2 Hz, 1H), 6.74 (dd, J=11.0 Hz, J=17.6 Hz, 1H), 6.64 (br s, 1H), 5.73 (dd, J=1.0 Hz, J=17.6 Hz, 1H), 5.15 (dd, J=1.0 Hz, J=11.0 Hz, 1H), 2.61 (s, 3H).

Example 68

6-(5-Chloro-2-methyl-phenyl)-N-(4-fluoromethyl-phenyl)-[1,3,5]-triazine-2,4-diamine To a solution of the title compound of Example 41 (0.185 g, 0.48 mmol) in dichloromethane (3 ml) and tetrahydrofuran (15 ml), cooled at −78° C., was added (diethylamino)sulfur trifluoride (0.081 g). After stirring at −78° C. for 2 hours, the mixture was treated with water (50 ml) and extracted with ethyl acetate (3×30 ml). The combined extracts were washed with water (25 ml), dried over anhydrous magnesium sulfate, and concentrated under reduced pressure. The residue was purified by preparative thin layer chromatography eluting with 20% ethyl acetate-hexane to provide the title compound (23 mg, 14% yield). $^1$H NMR (CDCl$_3$) δ 7.8 (d, 1H), 7.64 (d, 2H), 7.39-7.20 (m, 4H), 5.3-5.43 (d, 2H), 5.35 (br s, 2H), 2.56 (s, 3H).

Example 69

1-{4-[4-Amino-6-(5-chloro-2-ethoxy-phenyl)-)-[1,3,5]triazin-2-ylamino]-phenyl}-ethane-1,2-diol The reaction of 2,4-dichloro-6-(5-chloro-2-ethoxy-phenyl)-[1,3,5]triazine and 4-vinylphenylamine using the method described in Example 67 provided 6-(5-chloro-2-ethoxy-phenyl)-N-(4-vinyl-phenyl)-[1,3,5]triazine-2,4-diamine.

A mixture of 6-(5-chloro-2-ethoxy-phenyl)-N-(4-vinyl-phenyl)-[1,3,5]triazine-2,4-diamine (150 mg, 0.52 mmol), acetone (15 ml), water (5 ml), 4-methyl-morpholin-4-ol (50% in water, 1 ml), and potassium osmate dihydrate (5 mg, 0.01 mmol) was stirred for 12 hours. The mixture was concentrated under reduced pressure. The residue was purified by flash chromatography eluting with hexane-ethyl acetate (1:3) followed by ethyl acetate to provide the title compound (120 mg, 55% yield). $^1$H NMR (DMSO-d$_6$) δ 9.52 (br s, 1H), 7.73 (d, J=8.6 Hz, 2H), 7.50 (br s, 1H), 7.44 (dd, J=2.7 Hz, J=8.8 Hz, 1H), 7.22 (d, J=8.5 Hz, 2H), 7.15-7.05 (m 3H), 5.11 (br s, 1H), 4.66 (br s, 1H), 4.48 (br s, 1H), 4.08 (q, J=6.9 Hz, 2H), 3.40 (br s, 2H), 1.49 (t, J=6.9 Hz, 3H).

Example 70

Succinic acid mono-{4-[4-amino-6-(5-chloro-2-methyl-phenyl)-[1,3,5]triazin-2-ylamino]-benzyl ester A mixture of the title compound of Example 41 (0.684 g, 2.0 mmol), succinic anhydride (0.25 g, 2.5 mmol), N,N-diisopropylethylamine (0.387 g, 3 mmol), dimethylformamide (5 ml), and ethyl acetate (10 ml) was heated at 70° C. for 12 hours. The mixture was treated with ethyl acetate (150 ml) and cold hydrochloric acid (1 M, 50 ml). The organic layer was dried over anhydrous magnesium sulfate and concentrated under reduced pressure. The residue was purified by flash chromatography on silica gel eluting with 20% hexane-ethyl acetate to provide the title compound (0.34 g, 38% yield). $^1$H NMR (CD$_3$OD) δ 7.68-7.72 (m, 3H), 7-7.33 (m, 4H), 5.22 (s, 2H) 2.56-2.62 (m, 4H), 2.47 (s, 3H).

Example 71

Amino-acetic acid 4-[4-amino-6-(5-chloro-2-methyl-phenyl)-[1,3,5]triazin-2ylamino]-benzyl ester A mixture of the title compound of Example 41 (0.684 g, 2.0 mmol), N-tert-butoxycarbonyl glycine (0.368 g, 2.1 mmol), N,N-dimethylaminopyridine (0.049 g, 0.4 mmol), dimethylformamide (15 ml), and N,N-diisopropylcarbodiimide (0.278 g, 2.2 mmol) was stirred for 12 hours. The mixture was concentrated under reduced pressure. The residue was purified by flash chromatography eluting with 40% ethyl acetate-hexane to provide 2-tert-butoxycarbonylamino-acetic acid 4-[4-amino-6-(5-chloro-2-methyl-phenyl)-[1,3,5]triazin-2yl-amino]-benzyl ester (1.05 g, 100% yield). $^1$H NMR (CDCl$_3$) δ 7.74 (s, 1H), 7.63-7.74 (d, 1H), 7.6 (br s, 2H), 7.31-7.36 (m, 4H), 7.20-7.22 (d, 1H), 5.3-5.6 (br s, 2H), 5.17 (d, 2H) 4.95-5.1 (br s, 1H), 3.965 (d, 2H), 2.55 (s, 3H), 1.47 (s, 9H).

A mixture of 2-tert-butoxycarbonylamino-acetic acid 4-[4-amino-6-(5-chloro-2-methyl-phenyl)-[1,3,5]triazin-2yl-amino]-benzyl ester (1.0 g, 2 mmol), dichloromethane (20 ml), and a solution of hydrogen chloride in 1,4-dioxane (4 M, 5 ml) was stirred for 12 hours. The reaction mixture was poured into ethyl acetate (100 ml). The solid filtered and dried under reduced pressure to provide the hydrochloride salt of the title compound (0.38 g, 84% yield). $^1$H NMR (CD$_3$OD) δ7.75-8 (br s, 2H), 7.74 (s, 1H), 7.56-7.43 (m, 6H), 5.36 (s, 2H) 3.67 (s, 2H) 2.58 (s, 3H).

Example 72

(S)-2-Amino-Succinic acid 1-{4-[4-amino-6-(5-chloro-2-methyl-phenyl)-[1,3,5]triazin-2-ylamino]-benzyl}ester The title compound was synthesized according to the method described in Example 71 using the title compound of Example 41 and N-butoxycarbonyl aspartic acid γ-tert-butyl ester (75% yield). $^1$H NMR (CD$_3$OD) δ7.6-7.99 (br s, 2H), 7.63-7.33 (m, 7H), 5.18-5.26 (m, 2H) 4.3 (t, 1H) 2.90-2.96 (m, 2H), 2.47 (s, 3H).

Example 73

(S)-2-Amino-succinic acid 4-{4-[4-amino-6-(5-chloro-2-methyl-phenyl)-[1,3,5]triazin-2-ylamino]-benzyl}ester The title compound was synthesized according to the method described in Example 71 using the title compound of Example 41 and N-butoxycarbonyl aspartic acid α-tert-butyl ester (81% yield). $^1$H NMR (CD$_3$OD) δ 7.79-7.88 (br s, 2H), 7.69-7.79 (d, 1H), 7.54-7.39 (m, 6H), 5.20 (s, 2H) 4.31-4.34 (t, 1H) 3.06-3.08 (m, 2H), 2.53 (s, 3H).

Example 74

{4-[4-(5-Chloro-2-methyl-phenyl)-6-methylamino-[1,3,5]-triazin-2-ylamino]-phenyl}-methanol The reaction of 2,4-dichloro-6-(5-chloro-2-methyl-phenyl)-[1,3,5]triazine and 4-aminobenzyl alcohol using the method described in Example 67 and using methylamine in place of ammonia provided the title compound (81% yield). $^1$H NMR (acetone-d$_6$) δ 8.75, 8.62 (2br s, 1H), 8.02-7.82 (m, 3H), 7.41-7.28 (m, 4H), 6.83 (br s, 1H), 4.62-4.59 (m, 2H), 4.10-4.05 (m, 1H), 3.05, 3.01 (2 s, 3H), 2.67, 2.59 (2 s, 3H).

Example 75

(S)-2-Amino-5-guanidino-pentanoic acid 4-[4-amino-6-(5-chloro-2-methyl-phenyl)-[1,3,5]triazin-2-ylamino]-benzyl ester The title compound was synthesized according to the method described in Example 71 using the title compound of Example 41 and N-tert-butoxycarbonylamino-5-(N$^g$, N$^g$-di-tert-butoxycarbonyl)-L-arginine (54% yield). $^1$H NMR (CD$_3$OD) δ 7.9-7.7 (br s, 2H), 7.70 (s, 1H), 7.56-7.41 (m, 6H), 5.31 (s, 2H) 4.15 (t, 1H) 3.22-3.30 (m, 2H), 2.54 (s, 3H) 1.5-2.1 (m, 4H).

Example 76

(S)-Pyrrolidine-2-carboxylic acid 4-[4-amino-6-(5-chloro-2-methyl-phenyl)-[1,3,5]triazin-2-ylamino]-benzyl ester The title compound was synthesized according to the method described in Example 71 using the title compound of Example 41 and N-tert-butoxycarbonylamino-L-proline (79% yield). $^1$H NMR (CD$_3$OD) δ 7.4-7.99 (m, 7H), 5.30-5.20 (m, 2H) 4.46-4.47 (t, 1H) 2.90-3.4 (m, 2H), 2.52 (s, 3H), 2.4-2.52 (m, 1H) 2.1-2.5 (m, 4H).

Example 77

2-Amino-propionic acid 4-[4-amino-6-(5-chloro-2-methyl-phenyl)-[1,3,5]-triazin-2-ylamino]-benzyl ester The title compound was synthesized according to the method described in Example 71 using the title compound of Example 41 and N-tert-butoxycarbonylamino-L-alanine (73% yield). $^1$H NMR (CD$_3$OD) δ 7.4-7.99 (m, 8H), 5.30-5.20 (m, 2H) 4.10-4.14 (t, 1H) 2.52 (s, 3H), 1.52-1.54 (d, 3H).

Example 78

6-(5-Chloro-2-methyl-phenyl)-N-(4-methoxy-methyl-phenyl)-[1,3,5]triazine-2,4-diamine A mixture of (4-nitro-phenyl)-methanol (3.0 g, 19.6 mmol), potassium carbonate (3.9 g, 28.1 mmol), acetonitrile (100 ml), and iodomethane (11 ml, 176 mmol) was heated at 50° C. for 48 hours. The mixture was concentrated under reduced pressure and the residue was partitioned between ethyl acetate (100 ml) and saturated aqueous sodium chloride solution (100 ml). The organic layer was concentrated under reduced pressure. The residue was purified by flash chromatography on silica gel eluting with hexane-dichloromethane (1:1 followed by 1:2) to yield 1-methoxymethyl-4-nitro-benzene (1.0 g, 31% yield).

A mixture of 1-methoxymethyl-4-nitro-benzene (1.0 g, 0.6 mmol), ethyl alcohol (20 ml), and 10% palladium on carbon (100 mg) was treated with hydrogen gas (40 psi) on a Parr shaker for 4 hours. The mixture was filtered through a pad of celite under suction. The filtrate was concentrated under reduced pressure to yield 4-methoxy-methyl-phenylamine (750 mg, 91% yield).

The reaction of 2,4-dichloro-6-(5-chloro-2-methyl-phenyl)-[1,3,5]triazine and 4-methoxymethylphenylamine using the method described in Example 37 provided the title compound (45 mg, 13% yield). $^1$H NMR (DMSO-$d_6$) 9.60 (br s, 1H), 7.77 (m, 1H), 7.44 (s, 2H), 7.40-7.43 (m, 2H), 7.32 (m, 1H), 7.21-7.23 (m, 4H), 4.34 (s, 2H), 3.26 (s, 3H), 2.52 (s, 3H).

Example 79

6-(5-Chloro-2-methoxy-phenyl)-N—P-tolyl-[1,3,5]triazine-2,4-diamine

The reaction of 1-(4-methyl-phenyl)biguanidine hydrochloride with methyl 5-chloro-2-methoxybenzoate using the method described in Example 2 provided the title compound (2.225 g, 49% yield). $^1$H NMR (DMSO-$d_6$) 9.52 (br s, 1H), 7.70 (d, J=8.4 Hz, 2H), 7.47-7.53 (m, 2H), 7.07-7.16 (m, 5H), 3.80 (s, 3H), 2.26 (s, 3H).

Example 80

6-(2-Bromo-5-chloro-phenyl)-N-(4-chloro-phenyl)-[1,3,5]triazine-2,4-diamine To a suspension of 2-bromo-5-chloro-benzoic acid (2.5 g, 10.6 mmol) in dichloromethane (50 ml) was added a solution of oxalyl chloride in dichloromethane (2 M, 6 ml, 12 mmol) followed by N,N-dimethylformamide (5 drops). After stirring for 30 minutes, methanol (10 ml) was added. After stirring for 3 hours, the mixture was concentrated under reduced pressure. The residue was partitioned between ethyl acetate (150 ml) and saturated aqueous potassium carbonate solution (100 ml). The organic layer was concentrated under reduced pressure. The residue was purified by flash chromatography on silica gel eluting with dichloromethane-hexane (1:2) to provide methyl 2-bromo-5-chloro-benzoate (2.1 g, 79% yield).

The reaction of 1-(4-chlorophenyl)biguanidine hydrochloride and methyl 2-bromo-5-chloro-benzoate using the method described in Example 2 provided the title compound (58% yield). $^1$H NMR (DMSO-$d_6$) 9.87 (br s, 1H), 7.86 (d, J=8.3 Hz, 2H), 7.76 (d, J=8.3 Hz, 1H), 7.66 (m, 1H), 7.49 (m, 1H), 7.40 (br s, 2H), 7.34 (d, J=8.8 Hz, 2H).

Example 81

N-(4-Chloro-phenyl)-6-(2-chloro-5-trifluoromethyl-phenyl)-[1,3,5]triazine-2,4-diamine To a suspension of 2-chloro-5-trifluoromethyl-benzoic acid (2.8 g, 12.5 mmol) in dichloromethane (50 ml) was added a solution of oxalyl chloride in dichloromethane (2 M, 7 ml, 14 mmol) followed by N,N-dimethylformamide (5 drops). After stirring for 2 hours, methanol (10 ml) was added. After stirring for 20 hours, the mixture was concentrated under reduced pressure. The residue was partitioned between ethyl acetate (200 ml) and saturated aqueous potassium carbonate solution (100 ml). The organic layer was dried over sodium sulfate and concentrated under reduced pressure to provide methyl 2-chloro-5-trifluoromethyl-benzoate (2.6 g, 87% yield).

The reaction of 1-(4-chlorophenyl)biguanidine hydrochloride and methyl 2-chloro-5-trifluoromethyl-benzoate using the method described in Example 2 provided the title compound (34% yield). $^1$H NMR (DMSO-$d_6$) 9.89 (br s, 1H), 8.01 (m, 1H), 7.81-7.88 (m, 4H), 7.45 (d, 2H), 7.35 (d, J=8.9 Hz, 2H).

Example 82

N-Benzo[1.3]dioxol-5-yl-6-(2,5-dichloro-phenyl)-[1,3,5]triazine-2,4-diamine The reaction of 2,4-dichloro-6-(2,5-dichloro-phenyl)-[1,3,5]triazine and 3,4-(methylenedioxy)-aniline using the method described in Example 37 provided the title compound (8% yield). $^1$H NMR (DMSO-$d_6$) 9.63 (br s, 1H), 7.70 (s, 1H), 7.54-7.60 (m, 3H), 7.30 (br s, 2H), 7.09 (s, 1H), 6.85 (d, J=8.3 Hz, 1H), 5.60 (s, 2H).

Example 83

6-(2-Chloro-5-methyl-phenyl)-N-(4-chloro-phenyl)-[1,3,5]triazine-2,4-diamine To a suspension of 2-chloro-5-methyl-benzoic acid (3.0 g, 17.6 mmol) in dichloromethane (50 ml) was added a solution of oxalyl chloride in dichloromethane (2 M, 10 ml, 20 mmol) followed by N,N-dimethylformamide (5 drops). After stirring for 1 hour, methanol (20 ml) was added. After stirring for 3 hours, the mixture was concentrated under reduced pressure. The residue was partitioned between ethyl acetate (200 ml) and saturated aqueous potassium carbonate solution (100 ml). The organic layer was concentrated under reduced pressure to provide methyl 2-chloro-5-methyl-benzoate (3.2 g, 100% yield).

The reaction of 1-(4-chlorophenyl)biguanidine hydrochloride and methyl 2-chloro-5-methyl-benzoate using the method described in Example 2 provided the title compound (40% yield). $^1$H NMR (DMSO-$d_6$) 9.80 (br s, 1H), 7.87 (d, J=8.6 Hz, 2H), 7.40-7.43 (m, 2H), 7.27-7.33 (m, 5H), 2.34 (s, 3H).

Example 84

[4-Chloro-6-(5-chloro-2-methyl-phenyl)-[1,3,5]triazin-2-yl]-(1H-indazol-5-yl)-amine The reaction of 2,4-dichloro-6-(5-chloro-2-methyl-phenyl)-[1,3,5]triazine and 5-aminoindazole using the method described in Example 37 provided the title compound (7% yield). $^1$H NMR (DMSO-d$_6$) 12.95 (s, 1H), 9.52 (br s, 1H), 8.25 (s, 1H), 7.94 (s, 1H), 7.75 (m, 1H), 7.52 (m, 2H), 7.35-7.45 (m, 3H), 7.30 (m, 1H), 7.12)br s, 2H), 2.50 (s, 3H).

Example 85

6-(5-Chloro-2-fluoro-phenyl)-N-(4-chloro-phenyl)-[1,3,5]triazine-2,4-diamine

To a suspension of 5-chloro-2-fluoro-benzoic acid (2.0 g, 11.5 mmol) in dichloromethane (50 ml) was added a solution of oxalyl chloride in dichloromethane (2 M, 6.5 ml, 13 mmol) followed by N,N-dimethylformamide (5 drops). After stirring for 1 hour, methanol (10 ml) was added. After stirring for 20 hours, the mixture was concentrated under reduced pressure. The residue was partitioned between ethyl acetate (200 ml) and saturated aqueous potassium carbonate solution (100 ml). The organic layer was dried over sodium sulfate and concentrated under reduced pressure to provide methyl 5-chloro-2-fluoro-benzoate (2.0 g, 92% yield).

The reaction of 1-(4-chlorophenyl)biguanidine hydrochloride and methyl 5-chloro-2-fluoro-benzoate using the method described in Example 2 provided the title compound (50% yield). $^1$H NMR (DMSO-d6) 9.80 (br s, 1H), 7.98 (m, 1H), 7.88 (d, J=8.7 Hz, 2H), 7.62 (m, 1H), 7.30-7.40 (m, 5H).

Example 86

6-(2-Bromo-5-methyl-phenyl)-N-(4-chloro-phenyl)-[1,3,5]triazine-2,4-diamine

To a suspension of 2-bromo-5-methyl-benzoic acid (3.0 g, 14 mmol) in dichloromethane (100 ml) was added a solution of oxalyl chloride in dichloromethane (2 M, 8 ml, 16 mmol) followed by N,N-dimethylformamide (5 drops). After stirring for 30 minutes, methanol (15 ml) was added. After stirring for 3 hours, the mixture was concentrated under reduced pressure. The residue was partitioned between ethyl acetate (200 ml) and saturated aqueous potassium carbonate solution (100 ml). The organic layer was concentrated under reduced pressure to provide methyl 2-bromo-5-methyl-benzoate (3.2 g, 99% yield).

The reaction of 1-(4-chlorophenyl)biguanidine hydrochloride and methyl 2-bromo-5-methyl-benzoate using the method described in Example 2 provided the title compound (43% yield). $^1$H NMR (DMSO-d$_6$) 9.79 (br s, 1H), 7.85 (d, J=8.8 Hz, 2H), 7.57 (d, J=8.2 Hz, 1H), 7.38 (s, 1H), 7.25-7.30 (m, 4H), 7.20 (m, 1H), 2.31 (s, 3H).

Example 87

4-[4-Amino-6-(5-chloro-2-methyl-phenyl)-[1,3,5]triazin-2-ylamino]-benzaldehyde

To a suspension of the title compound of Example 41 (375 mg, 1.1 mmol) in dichloromethane (100 ml) was added pyridinium chlorochromate (810 mg, 2.7 mmol) and crushed molecular sieves (1.25 g, 3A). After stirring for 6 hours, diethyl ether (150 ml) was added and the mixture was filtered through a pad of silica gel under suction. The filtrate was concentrated under reduced pressure and purified by flash chromatography on silica gel eluting with ethyl acetate-hexane (1:3 followed by 1:2 followed by 1:1) to provide the title compound (25 mg, 7% yield). $^1$H NMR (DMSO-d$_6$) 10.10 (s, 1H), 9.86 (s, 1H), 8.07 (d, J=8.6 Hz, 2H), 7.84 (d, J=8.6 Hz, 2H), 7.79 (s, 1H), 7.43 (m, 2H), 7.34 (m, 2H), 2.53 (s, 3H).

Example 88

N-(4-Chloromethyl-phenyl)-6-(5-chloro-2-methyl-phenyl)-[1,3,5]triazine-2,4-diamine A solution of the title compound of Example 41 (2.25 g, 6.6 mmol) and thionyl chloride (1.2 g; 10 mmol) in tetrahydrofuran (40 ml) was heated at reflux for 6 hours. The mixture was concentrated under reduced pressure and the residue was dissolved in ethyl acetate (100 ml). The solution was washed with 10% aqueous sodium bicarbonate solution (2×30 ml), washed with water (30 ml), dried over anhydrous magnesium sulfate, and concentrated under reduced pressure. The residue was purified by flash chromatography eluting with ethyl acetate-hexane (1:1) to provide the title compound (1.2 g, 50% yield). $^1$H NMR (CDCl$_3$) δ (ppm): 7.79 (s, 1H), 7.60-7.62 (d, 2H), 7.19-7.38 (m, 5H), 5.2-5.4 (br s, 2H), 4.6 (s, 2H), 2.55 (s, 3H).

Example 89

4-[4-Amino-6-(2,5-dichlorophenyl)-[1,3,5]triazin-2-ylamino]-benzonitrile

The reaction of 1-(4-cyano-phenyl)biguanidine hydrochloride with methyl 2,5-dichlorobenzoate using the method described in Example 2 provided the title compound (94 mg, 21% yield). $^1$H NMR (DMSO-d$_6$) 10.22 (br s, 1H), 8.07 (d, J=8.7 Hz, 2H), 7.77-7.72 (m, 3H), 7.63-7.49 (m, 4H).

Example 90

N-(3-Chlorophenyl)-6-(2,5-dichlorophenyl)-[1,3,5]triazine-2,4-diamine

The reaction of 1-(3-chlorophenyl)biguanidine hydrochloride and methyl 2,5-dichlorobenzoate using the method described in Example 2 provided the title compound (60 mg, 16% yield). $^1$H NMR (DMSO-d$_6$) 9.88 (br s, 1H), 8.03 (s, 1H), 7.72-7.76 (m, 1H), 7.55-7.61 (m, 2H), 7.45 (br s, 2H), 7.26-7.32 (m, 2H), 7.01-7.07 (m, 1H).

Example 91

LPAAT-β Assay

A. Production of Recombinant LPAAT-β for Assays

For the construction of Baculovirus expression vectors, the full-length human LPAAT-β cDNA was amplified by PCR from the DNA template pCE9. LPAAT-β (West et al., *DNA Cell Biol.* 16:691-701 (1997)) using the primers 5'-TGATATCCGA AGMGATCTT ATGGAGCTGT GGC-CGTGTC-3' (olpb1F; SEQ ID NO:1) and 5'-CAG-GCTCTAG ACTACTGGGC CGGCTGCAC-3' (olpb1R; SEQ ID NO:2). The ~870 bp fragment generated was reamplified by PCR using the primers 5' CCTACGTCG ACATGGMCA AAAATTGATA TCCGAAGAAG ATC-3' (olpb2F; SEQ ID NO:3) and 5'-CAGGCTCTAG ACT-ACTGGGC CGGCTGCAC-3' (olpb1R; SEQ ID NO:2). The ~890 bp fragment generated was then cleaved with Sal I and Xba I for insertion into pFastBac™ HTc vector (Life Technologies, Gaithersberg, Md.) between the Sal I and Xba I sites for the generation of the plasmid pFB.LPAAT-β. This plasmid was then transformed into *E. coli* DH10Bac™ (Life Technologies, Gaithersberg, Md.) for the generation of recombinant Bacmid DNA for transfection into HighFive (Invitrogen, San Diego, Calif.) or SF9 insect cells for the production of recombinant Baculovirus stocks using the protocol described in the Bac-to-Bac® Baculovirus Expression System (Life Technologies, Gaithersberg, Md.), a eukaryotic expression system for generating recombinant baculovirus through site-specific transposition in *E. coli*. Viral stocks harvested from the transfected cells can then be used to infect fresh insect cells for the subsequent expression of LPAAT-β fusion protein with a poly-histidine tag and a myc-epitope near its N-terminus. The membrane fraction from these Sf9 cells would be the source of LPAAT enzyme.

B. Preparation of Cell Membranes from Sf9 Cells

For the preparation of membranes from Sf9 Cells, all steps are performed on ice or at 4° C. Sf9 cell pellets (~$10^8$ cells) were thawed and resuspended in 1-2 ml of buffer A (20 mM Hepes, pH 7.5, 1 mM DTT, 1 mM EDTA, 20% w/v glycerol, 1 mM Benzamidine, 1 µg/ml soybean trypsin inhibitor (SBTI), 1 µg/ml pepstatin A) w/o DTT but with 1 mM Pefabloc. The cells were lysed by sonication using a Branson Sonifier at output=2, duty cycle=2, 10 pulses each at 10s. with the tip of small sonicator probe submerged but not touching the walls. DTT was then added to 1 mM from a 1 M stock. The samples were centrifuged at 1500 rpm for 5 min. The low speed supernatant was saved and centrifuged (TLA 100.3 rotor, polycarbonate tubes, 2 ml/tube or 1.5 ml/tube minimum) at 100000×g for 1 hr. The high speed pellet was resuspend in Buffer A with a probe sonicator (10 pulses @ output #2 and duty cycle 20%) as a source of LPAAT enzyme.

C. Assay of LPAAT-β Activity

LPAAT-β catalyzes the transfer of an acyl group from a donor such as acyl-CoA to LPA. The transfer of the acyl group from acyl-CoA to LPA leads to the release of free CoA, which can be reacted with the thiol reagent, 5,5'-dithiobis(2-nitrobenzoic acid) (DTNB). The reaction between DTNB and the free sulfhydryl group from CoA generates a yellow-colored product, 3-carboxylato-4-nitrothiophenolate (CNP), that absorbs at 413 nm. LPAAT-β derived from Sf9 cell membrane overexpressing LPAAT-β were resuspended in HEPES saline buffer (20 mM HEPES pH 7.5, 150 mM NaCl), 1 mg/ml BSA and 72 µl aliquots were distributed into 96-well microtiter plates. 8 µl of compound of interest at 200 µM dissolved in 100% DMSO was added into each well. 20 µl of 1 mM 18:1-CoA and 1 mM sn-1-18:1 lysoPA was then added to each well to initiate the reaction and allowed to run at room temperature for 25 min. 100 µl of 1 mM DTNB in 100% ethanol was then added to each well to quench the reaction and for color development. The absorbance at 405 nm, measured using a spectrophotometer plate reader, is proportional to the activity of LPAAT-β in the sample. This colorimetric assay was used for the high throughput screening of LPAAT inhibitors. Compounds that showed >50% inhibition of the change in absorbance at 405 nm compared to control were selected for a secondary assay.

A secondary assay for LPAAT activity in cell extracts based on either the conversion of fluorescent NBD-LPA to NBD-PA (West, et al., *DNA Cell Biol.* 6:691-701, 1997) or [$^{14}$C]LPA to [$^{14}$C]PA using TLC analysis was used to screen compounds that showed >50% inhibition of LPAAT activity in the primary colorimetric assay. The radiometric assay was carried out in Sf9 cell membrane overexpressing LPAAT-β resuspended in HEPES-saline buffer, pH 7.5, 1 mg/ml BSA, 1 mM EDTA and 200 µM [$^{14}$C]18:1-CoA and 200 µM sn-1-18:1 lysoPA. The samples were incubated 7 min at 37° C., extracted into organic solvent ($CHCl_3/CH_3OH/HCl$ at 33/66/1), before loading onto TLC plates. A more detailed protocol for the radiometric assay is described below:

Specifically, this LPAAT assay is a modification of the acyltransferase assay published previously (Hollenback and Glomset, *Biochemistry* 37:363-376 (1999)).

1. The basic assay, in a total volume of 50 µl, employs a solution of substrates and the protein sample. Total assay volume, as well as the volume of each solution, can be changed to fit an experiment. In addition, other compounds, ex inhibitors and activators, can be included in the assay as well.

2. To prepare the solution of substrates:

a. Stocks of Hepes (pH 7.5), NaCl, EDTA, BSA and acyl-CoA (from Serdery or Sigma) are mixed with water to make the appropriate concentration of each compound. This can be varied from assay-to-assay, but the final reaction mix is about 50 mM Hepes, 100 mM NaCl, 1 mM EDTA, 1 mg/ml BSA and 0-400 µM acyl-CoA.

b. The lysoPA (from Avanti) is typically stored in chloroform and the $^{14}$C-labeled acyl-CoA (from Amersham) is typically stored in water/ethanol=1:1. Appropriate amounts of each solution are added the to a 12×75 mm borosilicate glass test tube and dry the solvent under $N_2$ or Ar. An appropriate volume of the solution prepared in 2a is added to the lysoPA and $^{14}$C-labeled acyl-CoA. The lipids are resuspend by sonication for 15 sec in a bath sonicator. The resulting suspension is then incubated (with occasional gentle vortexing) for about 10 minutes at room temp. The sn-1-16:0 lysoPA may require brief warming of the solvent to solubilize it. The concentration of lysoPA and $^{14}$C-labeled acyl-CoA can vary, but typically the final lysoPA concentration ranges between 0 and 400 µM and the $^{14}$C-labeled acyl-CoA specific activity ranges between 0.5 and 2 Ci/mol.

3. Protein sample: varies from experiment-to-experiment.

4. The assay is performed by mixing the components in 12×75 mm borosilicate glass test tubes (the order of addition does not matter unless indicated) and incubating at 37° C. for 5 to 10 minutes such that the assay within the linear range for time and protein.

5. The reaction is quenched by adding 1.3 ml of chloroform/methanol/HCl=48/51/0.7 and vortexing. 10 µl of carrier solution is then added (3 mg/ml each PA, ex. 16:0-18:1, and lysoPA, ex sn-1-18:1, in chloroform). Two phases are formed by adding 0.3 ml of water to each tube and vortexing.

6. The sample is centrifuged for 3 minutes at 1000×g, the upper (aqueous/methanol) phase is aspirated and the lower phase is dried under nitrogen.

7. Thin layer chromatography:

a. The dried samples are resuspended in 50 µl of chloroform and a 15 µl aliquot is immediately spotted on an Analtech silica gel 60HP-TLC plate (10×20 cm).

b. Plates are developed in chloroform/methanol/acetic acid/water=85/12.5/12.5/3 (takes about 15 min) and dried.

c. To be able to convert pixel volume (determined by the Storm phosphor imager, see step 8b) into cpm, cpm standard curve must be generated on the plate. $^{14}$C-labeled oleate dilutions in chloroform are made for this purpose. Four stocks (50 cpm/μl to 800 cpm/μl) are made and 2 μl of a different concentration are spotted in each corner of the plate (where previously there was no radioactivity).

d. For quality control purposes, the plates are stained with primuline and scanned with the Storm (blue chemilluminescence mode).

The PA and lysoPA bands are easily detected in this system because of the carrier added in step 5. PA and lysoPA have respective Rf's of about 0.63 and 0.21.

8. Quantitating activity:

a. The plates are then wrapped in saran wrap and exposed to a freshly blanked phosphor screen overnight (longer exposures can also be done to increase the signal).

b. The screens are scanned (Phosphorimager mode), and LPAAT activity is determined by quantifying the pixels in the band comigrating with PA standard versus the standard curve generated from the cpm standards that were spotted in step 7c.

TABLE 1

| | Compound | LPAAT-β Cell-Free Assay (IC50, μM) | Compound Name |
|---|---|---|---|
| 1 | | 0.057 | 6-(5-Chloro-2-methoxyphenyl)-N-(4-chlorophenyl)-[1,3,5]triazine-2,4-diamine |
| 2 | | 2.30 | 6-(5-Chloro-2-methoxyphenyl)-N-phenyl-[1,3,5]triazine-2,4-diamine |
| 3 | | 0.022 | 6-(5-Chloro-2-methoxyphenyl)-N-(4-nitrophenyl)-[1,3,5]triazine-2,4-diamine |
| 4 | | 0.050 | 6-(2,5-Dichlorophenyl)-N-(4-chlorophenyl)-[1,3,5]triazine-2,4-diamine |

TABLE 1-continued

| | Compound | LPAAT-β Cell-Free Assay (IC50, μM) | Compound Name |
|---|---|---|---|
| 5 | | 0.280 | N-Benzo[1,3]dioxol-5-yl-6-(5-chloro-2-methoxyphenyl)-[1,3,5]triazine-2,4-diamine |
| 6 | | 0.230 | N-(4-Chlorophenyl)-6-(2-fluoro-5-methoxyphenyl)-[1,3,5]triazine-2,4-diamine |
| 7 | | 0.140 | 6-(5-Chloro-2-ethoxyphenyl)-N-(4-Chlorophenyl)-[1,3,5]triazine-2,4-diamine |
| 8 | | 0.140 | 6-(5-Chloro-2-methoxyphenyl)-N-(3,4-dichlorophenyl)-[1,3,5]triazine-2,4-diamine |
| 9 | | 0.055 | 6-(5-Chloro-2-methylphenyl)-N-(4-Chlorophenyl)-[1,3,5]triazine-2,4-diamine |

TABLE 1-continued

| | Compound | LPAAT-β Cell-Free Assay (IC50, μM) | Compound Name |
|---|---|---|---|
| 10 | (structure) | 0.076 | N-2-(4-Bromophenyl)-6-(5-chloro-2-methoxyphenyl)-[1,3,5]triazine-2,4-diamine |
| 11 | (structure) | 0.060 | N-2-(4-Bromophenyl)-6-(5-chloro-2-methylphenyl)-[1,3,5]triazine-2,4-diamine |
| 12 | (structure) | 0.070 | N-2-(4-Bromophenyl)-6-(2,5-dichlorophenyl)-[1,3,5]triazine-2,4-diamine |
| 13 | (structure) | 0.055 | 6-(5-chloro-2-methyl-phenyl)-n-(1h-indazol-6-yl)-[1,3,5]triazine-2,4-diamine |
| 14 | (structure) | 0.250 | N-(4-chlorophenyl)-6-(2,5-dimethylphenyl)-[1,3,5]triazine-2,4-diamine |

TABLE 1-continued

| | Compound | LPAAT-β Cell-Free Assay (IC50, μM) | Compound Name |
|---|---|---|---|
| 15 | | 0.430 | 6-(5-chloro-2-methoxyphenyl)-N-(4-fluorophenyl)-[1,3,5]triazine-2,4-diamine |
| 16 | | 0.800 | N-(4-chlorophenyl)-6-(3-chlorophenyl)-[1,3,5]triazine-2,4-diamine |
| 17 | | 1.00 | N-(4-chlorophenyl)-6-(2,5-dimethoxyphenyl)-[1,3,5]triazine-2,4-diamine |
| 18 | | prodrug | Poly-(L-glutamic acid) conjugate of 4-[4-chloro-6-(5-chloro-2-methyl-phenyl)-[1,3,5]-triazin-2-ylamino]-phenyl}-methanol |
| 19 | | 0.2 | N-Benzo[1.3]dioxol-5-yl-6-(5-chloro-2-methyl-phenyl)-[1,3,5]triazine-2,4-diamine |

TABLE 1-continued

| Compound | | LPAAT-β Cell-Free Assay (IC50, μM) | Compound Name |
|---|---|---|---|
| 20 | [structure] | 0.01 | (4-Bromo-phenyl)-[4-chloro-6-(5-chloro-2-methyl-phenyl)-[1,3,5]triazin-2-yl]-amine |
| 21 | [structure] | 0.2 | (4-Bromo-phenyl)-[4-(5-chloro-2-methyl-phenyl)-6-methoxy-[1,3,5]triazin-2-yl-amine |
| 22 | [structure] | 0.013 | [4-(5-Chloro-2-methyl-phenyl)-6-methyl-[1,3,5]triazin-2-yl]-(1H-indazol-6-yl)-amine |
| 23 | [structure] | 0.014 | (4-Bromo-phenyl)-[4-(5-chloro-2-methyl-phenyl)-6-methyl-[1,3,5]triazin-2-yl-amine |
| 24 | [structure] | 0.7 | (4-Bromo-phenyl)-[4-(5-chloro-2-methyl-phenyl)-6-ethyl-[1,3,5]triazin-2-yl-amine |

TABLE 1-continued

| | Compound | LPAAT-β Cell-Free Assay (IC50, μM) | Compound Name |
|---|---|---|---|
| 25 | | 10 | 6-(5-Chloro-2-methyl-phenyl)-N-(4-chloro-phenyl)-N-methyl-[1,3,5]triazine-2,4-diamine |
| 26 | | 0.004 | [4-Chloro-6-(5-chloro-2-methyl-phenyl)-[1,3,5]triazin-2-yl]-(1H-indazol-6-yl)-amine |
| 27 | | 2.7 | [2-Aminimethyl-6-(5-chloro-2-methyl-phenyl)-[1,3,5]triazin-4-yl]-(4-bromo-phenyl)-amine |
| 28 | | 0.42 | 6-(5-Chloro-2-methyl-phenyl)-(4-bromo-phenyl)-[1,3,5]-triazine-2-carbonitrile |
| 29 | | 1.1 | (4-Bromo-phenyl)-[4-(5-chloro-2-methyl-phenyl)-6-methylsulfanyl-[1,3,5]triazin-2-yl]-amine |

TABLE 1-continued

| | Compound | LPAAT-β Cell-Free Assay (IC50, μM) | Compound Name |
|---|---|---|---|
| 30 | | 0.01 | [6-(5-Chloro-2-methyl-phenyl)-2-chloro-3-yl-[1,3,5]-triazin-4-yl]-(4-nitro-phenyl)-amine |
| 31 | | 6 | [6-(5-Chloro-2-methyl-phenyl)-2-piperidin-3-yl-[1,3,5]triazin-4-yl]-(4-chloro-phenyl)-amine |
| 32 | | 10 | 6-(5-Chloro-2-methyl-phenyl)-N-(4-chloro-phenyl)-N,N-dimethy-[1,3,5]triazine-2,4-diamine |
| 33 | | 0.24 | [6-(5-Chloro-2-methyl-phenyl)-[1,3,5]triazin-4-yl]-(4-chloro-phenyl)-amine |
| 34 | | 0.16 | N-(4-Chloro-3-methylamino-phenyl)-6-(5-chloro-2-methyl-phenyl)-[1,3,5]triazine-2,4-diamine |

TABLE 1-continued

| | Compound | LPAAT-β Cell-Free Assay (IC50, μM) | Compound Name |
|---|---|---|---|
| 35 | | 0.13 | [6-(5-Chloro-2-methyl-phenyl)-2-chloro-3-yl-[1,3,5]-triazin-4-yl]-(4-azido-phenyl)-amine |
| 36 | | 0.88 | 6-(5-Chloro-2-methyl-phenyl)-N-(4-azido-phenyl)-amino-[1,3,5]triazine-2,4-diamine |
| 37 | | 0.59 | 6-(5-Chloro-2-methyl-phenyl)-N-indan-5-yl-[1,3,5]triazine-2,4-diamine |
| 38 | | 1 | 6-(5-Chloro-2-methyl-phenyl)-N-(4-ethyl-phenyl)-[1,3,5]triazine-2,4-diamine |
| 39 | | 0.32 | 6-(5-Chloro-2-methyl-phenyl)-N-p-tolyl-[1,3,5]triazine-2,4-diamine |

TABLE 1-continued

| Compound | | LPAAT-β Cell-Free Assay (IC50, μM) | Compound Name |
|---|---|---|---|
| 40 | (structure) | 2.6 | N-(4-bromophenyl)-6-(5-chloro-2-trifluoromethylphenyl)-[1,3,5]triazine-2,4-diamine |
| 41 | (structure) | 0.15 | {4-[4-Chloro-6-(5-chloro-2-methyl-phenyl)-[1,3,5]triazin-2-ylamino]-phenyl}-methanol |
| 42 | (structure) | 0.28 | 6-(5-Chloro-2-methyl-phenyl)-N-(4-ethynyl-phenyl)-[1,3,5]triazine-2,4-diamine |
| 43 | (structure) | 0.4 | 5-[4-amino-6-(5-chloro-2-methylphenyl)-[1,3,5]triazin-2-ylamino]-2-chloro-N-methylbenzamide |
| 44 | (structure) | 1.5 | 6-(5-chloro-2-methylaminophenyl)-N-(4-chlorophenyl)-[1,3,5]triazine-2,4-diamine |

TABLE 1-continued

| | Compound | LPAAT-β Cell-Free Assay (IC50, μM) | Compound Name |
|---|---|---|---|
| 45 | | 0.04 | 6-(5-Bromo-2-chloro-phenyl)-N-(4-chloro-phenyl)-[1,3,5]triazine-2,4-diamine |
| 46 | | 0.44 | {4-[4-Amino-6-(2,5-dichloro-phenyl)-[1,3,5]triazin-2-ylamino]-phenyl}-methanol |
| 47 | | 0.14 | 6-(5-chloro-2-dimethylaminophenyl)-N-(4-chlorophenyl)-[1,3,5]triazine-2,4-diamine |
| 48 | | 0.11 | 6-(2,5-Dichloro-phenyl)-N-(1H-indazol-6-yl)-[1,3,5]triazine-2,4-diamine |
| 49 | | 0.21 | 6-(2,5-Dichloro-phenyl)-N-p-tolyl-[1,3,5]triazine-2,4-diamine |

TABLE 1-continued

| Compound | | LPAAT-β Cell-Free Assay (IC50, μM) | Compound Name |
|---|---|---|---|
| 50 | | 0.2 | N-(4-Chloro-phenyl)-6-(5-chloro-2-propoxy-phenyl)-[1,3,5]triazine-2,4-diamine |
| 51 | | 0.6 | 6-(5-Chloro-2-ethoxy-phenyl)-N-(1H-indazol-6-yl)-[1,3,5]triazine-2,4-diamine |
| 52 | | 0.62 | 6-(5-Chloro-2-isopropoxy-phenyl)-N-(4-chloro-phenyl)-[1,3,5]triazine-2,4-diamine |
| 53 | | 1.8 | {4-[4-Amino-6-(5-chloro-2-ethoxy-phenyl)[1,3,5]triazin-2-ylamino]-phenyl}-methanol |
| 54 | | 0.12 | 6-(5-chloro-2-ethoxyphenyl)-N-(4-nitrophenyl)-[1,3,5]triazine-2,4-diamine |

TABLE 1-continued

| | Compound | LPAAT-β Cell-Free Assay (IC50, μM) | Compound Name |
|---|---|---|---|
| 55 | | 0.8 | N-Benzo[1.3]dioxol-5-yl-6-(5-chloro-2-ethoxyphenyl)[1,3,5]triazine-2,4-diamine |
| 56 | | 0.44 | 6-(5-Chloro-2-ethoxyphenyl)-N-(4-nitrophenyl)-[1,3,5]triazine-2,4-diamine |
| 57 | | 0.14 | 2-{4-[4-Amino-6-(5-chloro-2-methyl-phenyl)-[1,3,5]triazin-2-ylamino]-phenyl}-ethanol |
| 58 | | 1.8 | 6-(5-Chloro-2-methyl-phenyl)-N-(4-dimethylaminomethyl-phenyl)-[1,3,5]triazine-2,4-diamine |
| 59 | | 0.4 | 6-(5-Chloro-2-methyl-phenyl)-N-(3,4-dimethyl-phenyl)-[1,3,5]triazine-2,4-diamine |

TABLE 1-continued

| | Compound | LPAAT-β Cell-Free Assay (IC50, µM) | Compound Name |
|---|---|---|---|
| 60 | | 1.3 | {4-[4-Amino-6-(5-chloro-2-methyl-phenyl)-[1,3,5]triazin-2-ylamino]-phenyl}-acetic acid |
| 61 | | 2.3 | 6-(5-Chloro-2-ethoxyphenyl)-N-p-tolyl-[1,3,5]triazine-2,4-diamine |
| 62 | | 1 | 5-[4-amino-6-(5-chloro-2-ethoxyphenyl)-[1,3,5]triazin-2-ylamino]-2-chloro-N-methylbenzamide |
| 63 | | 3.1 prodrug | (S)-2-Amino-pentanedioic acid 5-{4-[4-amino-6-(5-chloro-2-methyl-phenyl)-[1,3,5]triazin-2-ylamino]-benzyl} ester |
| 64 | | prodrug | (S)-2-Amino-pentanedioic acid 1-{4-[4-amino-6-(5-chloro-2-methyl-phenyl)-[1,3,5]-triazin-2-ylamino]-benzyl} ester |

TABLE 1-continued

| | Compound | LPAAT-β Cell-Free Assay (IC50, μM) | Compound Name |
|---|---|---|---|
| 65 | | 0.6 | 6-[5-Chloro-2-(2-methoxy-ethoxy)-phenyl]-N-(4-chloro-phenyl)[1,3,5]triazine-2,4-diamine |
| 66 | | 0.75 | 6-(5-Chloro-2-methyl-phenyl)-N-(3-ethyl-phenyl)-[1,3,5]triazine-2,4-diamine |
| 67 | | 0.71 | 6-(5-Chloro-2-methyl-phenyl)-N-(4-vinyl-phenyl)-[1,3,5] triazine-2,4-diamine |
| 68 | | 0.13 | 6-(5-Chloro-2-methyl-phenyl)-N-(4-fluoromethyl-phenyl)-[1,3,5]-triazine-2,4-diamine |
| 69 | | 2.6 | 1-{4-[4-Amino-6-(5-chloro-2-ethoxy-phenyl)-)-[1,3,5]triazin-2-ylamino]-phenyl}-ethane-1,2-diol |

TABLE 1-continued

| | Compound | LPAAT-β Cell-Free Assay (IC50, µM) | Compound Name |
|---|---|---|---|
| 70 | | 0.83 prodrug | Succinic acid mono-{4-[4-amino-6-(5-chloro-2-methyl-phenyl)-[1,3,5]triazin-2-ylamino]-benzyl ester |
| 71 | | 0.48 prodrug | Amino-acetic acid 4-[4-amino-6-(5-chloro-2-methyl-phenyl)-[1,3,5]triazin-2ylamino]-benzyl ester |
| 72 | | 1.4 prodrug | (S)-2-Amino-succinic acid 1-{4-[4-amino-6-(5-chloro-2-methyl-phenyl)-[1,3,5]triazin-2-ylamino]-benzyl} ester |
| 73 | | 2.1 prodrug | (S)-2-Amino-succinic acid 4-{4-[4-amino-6-(5-chloro-2-methyl-phenyl)-[1,3,5]triazin-2-ylamino]-benzyl} ester |
| 74 | | 0.68 | {4-[4-(5-Chloro-2-methyl-phenyl)-6-methylamino-[1,3,5]-triazin-2-ylamino]-phenyl}-methanol |

TABLE 1-continued

| | Compound | LPAAT-β Cell-Free Assay (IC50, μM) | Compound Name |
|---|---|---|---|
| 75 | | 0.97 prodrug | (S)-2-Amino-5-guanidino-pentanoic acid 4-[4-amino-6-(5-chloro-2-methyl-phenyl)-[1,3,5]triazin-2-ylamino]-benzyl ester |
| 76 | | 10 prodrug | (S)-Pyrrolidine-2-carboxylic acid 4-[4-amino-6-(5-chloro-2-methyl-phenyl)-[1,3,5]triazin-2-ylamino]-benzyl ester |
| 77 | | 1.3 prodrug | 2-Amino-propionic acid 4-[4-amino-6-(5-chloro-2-methyl-phenyl)-[1,3,5]-triazin-2-ylamino]-benzyl ester |
| 78 | | 0.64 | 6-(5-Chloro-2-methyl-phenyl)-N-(4-methoxy-methyl-phenyl)-[1,3,5]triazine-2,4-diamine |
| 79 | | 0.23 | 6-(5-Chloro-2-methoxy-phenyl)-N-p-tolyl-[1,3,5]triazine-2,4-diamine |

TABLE 1-continued

| | Compound | LPAAT-β Cell-Free Assay (IC50, μM) | Compound Name |
|---|---|---|---|
| 80 | | 0.14 | 6-(2-Bromo-5-chloro-phenyl)-N-(4-chloro-phenyl)-[1,3,5]triazine-2,4-diamine |
| 81 | | 0.1 | N-(4-Chloro-phenyl)-6-(2-chloro-5-trifluoromethyl-phenyl)-[1,3,5]triazine-2,4-diamine |
| 82 | | 0.3 | N-Benzo[1.3]dioxol-5-yl-6-(2,5-dichloro-phenyl)-[1,3,5]triazine-2,4-diamine |
| 83 | | 0.18 | 6-(2-chloro-5-methyl-phenyl)-N-(4-chloro-phenyl)-[1,3,5]triazine-2,4-diamine |
| 84 | | 0.1 | [4-Chloro-6-(5-chloro-2-methyl-phenyl)-[1,3,5]triazin-2-yl]-(1H-indazol-5-yl)-amine |

TABLE 1-continued

| | Compound | LPAAT-β Cell-Free Assay (IC50, μM) | Compound Name |
|---|---|---|---|
| 85 | | 0.07 | 6-(5-chloro-2-fluoro-phenyl)-N-(4-chloro-phenyl)-[1,3,5]triazine-2,4-diamine |
| 86 | | 0.45 | 6-(2-bromo-5-methyl-phenyl)-N-(4-chloro-phenyl)-[1,3,5]triazine-2,4-diamine |
| 87 | | 0.11 | 4-[4-Amino-6-(5-chloro-2-methyl-phenyl)-[1,3,5]triazin-2-ylamino]-benzaldehyde |
| 88 | | 0.18 | N-(4-Chloromethyl-phenyl)-6-(5-chloro-2-methyl-phenyl)-[1,3,5]triazine-2,4-diamine |
| 89 | | 0.1 | 4-[4-amino-6-(2,5-dichlorophenyl)-[1,3,5]triazin-2-ylamino]-benzonitrile |

TABLE 1-continued

| Compound | | LPAAT-β Cell-Free Assay (IC50, μM) | Compound Name |
|---|---|---|---|
| 90 | [structure: triazine with NH2, linked to 2,5-dichlorophenyl and NH-(3-chlorophenyl)] | 4.80 | N-(3-chlorophenyl)-6-(2,5-dichlorophenyl)-[1,3,5]triazine-2,4-diamine |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A method for treating a prostate, breast, lung, ovarian, brain, cervical, colon or bladder cancer in which lysophosphatidic acid acyltransferase β (LPAAT-β) activity is associated comprising administering to an animal in need, a compound or salt thereof, or in combination with a pharmaceutically acceptable carrier or diluent, in an amount effective to treat said cancer, wherein the compound is any one of compounds 6-(5-Chloro-2-methoxyphenyl)-N-(4-chlorophenyl)-[1,3,5]triazine-2,4-diamine; 6-(5-Chloro-2-

SEQUENCE LISTING

<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
tgatatccga agaagatctt atggagctgt ggccgtgtc                              39

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
caggctctag actactgggc cggctgcac                                         29

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
cctacgtcga catggaacaa aaattgatat ccgaagaaga tc                          42 methoxyphenyl)-N-phenyl-[1,3,5]triazine-2,4-diamine; 6-(5-Chloro-2-methoxyphenyl)-N-(4-nitrophenyl)-[1,3,5]triazine-2,4-diamine; N-Benzo[1,3]dioxol-5-yl-6-(5-chloro-2-methoxyphenyl)-[1,3,5]triazine-2,4-diamine; N-(4-Chlorophenyl)-6-(2-fluoro-5-methoxyphenyl)-[1,3,5]triazine-2,4-diamine; 6-(5-Chloro-2-ethoxyphenyl)-N-(4-Chlorophenyl)-[1,3,5]triazine-2,4-diamine; 6-(5-Chloro-2-methoxyphenyl)-N-(3,4-dichlorophenyl)-[1,3,5]triazine-2,4-diamine; 6-(5-Chloro-2-methylphenyl)-N-(4-Chlorophenyl)-[1,3,5]triazine-2,4-diamine; N-2-(4-Bromophenyl)-6-(5-chloro-2-methoxyphenyl)-[1,3,5]triazine-2,4-diamine; N-2-(4-Bromophenyl)-6-(5-chloro-2-methylphenyl)-[1,3,5]triazine-2,4-diamine; 6-(5-chloro-2-methyl-phenyl)-n-(1h-indazol-6-yl)-[1,3,5]triazine-2,4-diamine; N-(4-chlorophenyl)-6-(2,5-dimethylphenyl)-[1,3,5]triazine-2,4-diamine; 6-(5-chloro-2-methoxyphenyl)-N-(4-fluorophenyl)-[1,3,5]triazine-2,4-diamine; N-(4-chlorophenyl)-6-(3-chlorophenyl)-[1,3,5]triazine-2,4-diamine; N-(4-chlorophenyl)-6-(2,5-dimethoxyphenyl)-[1,3,5]triazine-2,4-diamine; Poly-(L-glutamic acid) conjugate of 4-[4-chloro-6-(5-chloro-2-methyl-phenyl)-[1,3,5]-triazin-2-ylamino]-phenyl}-methanol; N-Benzo[1,3]dioxol-5-yl-6-(5-chloro-2-methyl-phenyl)-[1,3,5]triazine-2,4-diamine; (4-Bromo-phenyl)-[4-chloro-6-(5-chloro-2-methyl-phenyl)-[1,3,5]triazin-2-yl]-amine; (4-Bromo-phenyl)-[4-(5-chloro-2-methyl-phenyl)-6-methoxy-[1,3,5]triazin-2-yl-amine; [4-(5-Chloro-2-methyl-phenyl)-6-methyl-[1,3,5]triazin-2-yl]-(1H-indazol-6-yl)-amine; (4-Bromo -phenyl)-[4-(5-chloro-2-methyl-phenyl)-6-methyl-[1,3,5]triazin-2-yl-amine; (4-Bromo-phenyl)-[4-(5-chloro-2-methyl-phenyl)-6-ethyl-[1,3,5]triazin-2-yl-amine; 6-(5-Chloro-2-methyl-phenyl) -N-(4-chloro-phenyl)-N-methyl-[1,3,5]triazine-2,4-diamine; [4-Chloro-6-(5-chloro-2-methyl-phenyl)-[1,3,5]triazin-2-yl]-(1H-indazo1-6-yl)-amine; [2-Aminimethyl-6-(5-chloro-2-methyl-phenyl)-[1,3,5]triazin-4-yl]-(4-bromo-phenyl)-amine; 6-(5-Chloro-2-methyl-phenyl)-(4-bromo-phenyl)-[1,3,5]-triazine-2-carbonitrile; (4-Bromo-phenyl)-[4-(5-chloro-2-methyl-phenyl)-6-methylsulfanyl-[1,3,5]triazin-2-yl]-amine; [6-(5-Chloro-2-methyl-phenyl)-2-chloro-3-yl-[1,3,5]-triazin-4-yl]-(4-nitro-phenyl)-amine; [6-(5-Chloro-2-methyl-phenyl)-2-piperidin-3-yl-[1,3,5]triazin-4-yl]-(4-chloro-phenyl)-amine; 6-(5-Chloro-2-methyl-phenyl)-N-(4-chloro-phenyl)-N,N-dimethy-[1,3,5]triazine-2,4-diamine; [6-(5-Chloro-2-methyl-phenyl)-[1,3,5]triazin-4-yl]-(4-chloro-phenyl)-amine; N-(4-Chloro-3-methylamino-phenyl)-6-(5-chloro-2-methyl-phenyl)-[1,3,5]triazine-2,4-diamine; [6-(5-Chloro-2-methyl-phenyl)-2-chloro-3-yl-[1,3,5]-triazin-4-yl]-(4-azido-phenyl)-amine; 6-(5-Chloro-2-methyl-phenyl)-N-(4-azido-phenyl)-amino-[1,3,5]triazine-2,4-diamine; 6-(5-Chloro-2-methyl-phenyl)-N-indan-5-yl-[1,3,5]triazine-2,4-diamine; 6-(5-Chloro-2-methyl-phenyl)-N-(4-ethyl-phenyl)-[1,3,5]triazine-2,4-diamine; 6-(5-Chloro-2-methyl-phenyl)-N-p-tolyl-[1,3,5]triazine-2,4-diamine; N-(4-bromophenyl)-6-(5-chloro-2-trifluoromethylphenyl)-[1,3,5]triazine-2,4-diamine; {4-[4-Chloro-6-(5-chloro-2-methyl-phenyl)-[1,3,5]triazin-2-ylamino]-phenyl}-methanol; 6-(5-Chloro-2-methyl-phenyl)-N-(4-ethynyl-phenyl)-[1,3,5]triazine-2,4-diamine; 5-[4-amino-6-(5-chloro-2-methylphenyl)-[1,3,5]triazin-2-ylamino]-2-chloro-N-methylbenzamide; 6-(5-chloro-2-methylaminophenyl)-N-(4-chlorophenyl)-[1,3,5]triazine-2,4-diamine; 6-(5-Bromo-2-chloro-phenyl)-N-(4-chloro-phenyl)-[1,3,5]triazine-2,4-diamine; 6-(5-chloro-2-dimethylaminophenyl)-N-(4-chlorophenyl)-[1,3,5]triazine-2,4-diamine; N-(4-Chloro-phenyl)-6-(5-chloro-2-propoxy-phenyl)-[1,3,5]triazine-2,4-diamine; 6-(5-Chloro-2-ethoxy-phenyl)-N-(1H-indazol-6-yl)-[1,3,5]triazine-2,4-diamine; 6-(5-Chloro-2-isopropoxy-phenyl)-N-(4-chloro-phenyl)-[1,3,5]triazine-2,4-diamine; {4-[4-Amino-6-(5-chloro-2-ethoxy-phenyl)[1,3,5]triazin-2-ylamino]-phenyl}-methanol; 6-(5-chloro-2-ethoxyphenyl)-N-(4-nitrophenyl)-[1,3,5]triazine-2,4-diamine; N-Benzo[1,3]dioxol-5-yl-6-(5-chloro-2-ethoxy-phenyl)[1,3,5]triazin-2-ylamino]-phenyl}-methanol; 6-(5-Chloro-2-ethoxyphenyl)-N-(4-nitrophenyl)-[1,3,5]triazine-2,4-diamine; 2-{4-[4-Amino-6-(5-chloro-2-methyl-phenyl)-[1,3,5]triazin-2-ylamino]-phenyl}-ethanol; 6-(5-Chloro-2-methyl-phenyl)-N-(4-dimethylaminomethyl-phenyl)-[13,5]triazine-2,4-diamine; 6-(5-Chloro-2-methyl-phenyl)-N -(3,4-dimethyl-phenyl)-[1,3,5]triazine-2,4-diamine; {4-[4-Amino-6-(5-chloro-2-methyl-phenyl)-[1,3,5]triazin-2-ylamino]-phenyl}-acetic acid; 6-(5-Chloro-2-ethoxyphenyl)-N-p-tolyl-[1,3,5]triazine-2,4-diamine; 5-[4-amino-6-(5-chloro-2-ethoxyphenyl)-[1,3,5]triazin-2-ylamino]-2-chloro-N-methylbenzamide; (S)-2-Amino-pentanedioic acid 5-{4-[4-amino-6-(5-chloro-2-methyl-phenyl)-[1,3,5 ]triazin-2-ylamino]-benzyl}ester; (S)-2-Amino-pentanedioic acid 1-{4-[4-amino-6-(5-chloro-2-methyl-phenyl)-[1,3,5]-triazin-2-ylamino]-benzyl}ester; 6-[5-Chloro-2-(2-methoxy-ethoxy)-phenyl]-N-(4-chloro-phenyl)[1,3,5]triazine-2,4-diamine; 6-(5-Chloro-2-methyl-phenyl)-N-(3-ethyl-phenyl)-[1,3,5]triazine-2,4-diamine; 6-(5-Chloro-2-methyl-phenyl) -N-(4-vinyl-phenyl)-[1,3,5]triazine-2,4-diamine; 6-(5-Chloro-2-methyl-phenyl)-N-(4-fluoromethyl-phenyl)-[1,3,5]-triazine-2,4-diamine; 1-{4-[4-Amino-6-(5-chloro-2-ethoxy-phenyl)-)-[1,3,5]triazin-2-ylamino]-phenyl}-ethane-1,2-diol; Succinic acid mono-{4-[4-amino-6-(5-chloro-2-methyl-phenyl)-[1,3,5]triazin-2-ylamino]-benzyl ester; Amino-acetic acid 4-[4-amino-6-(5-chloro-2-methyl-phenyl)-[1,3,5]triazin-2ylamino]-benzyl ester; (S)-2-Amino-succinic acid 1-{4-[4-amino-6-(5-chloro-2-methyl-phenyl)-[1,3,5]triazin-2-ylamino]-benzyl}ester; (S)-2-Amino-succinic acid 4-{4-[4-amino-6-(5-chloro-2-methyl-phenyl)-[1,3,5]triazin-2-ylamino]-benzyl}ester; (4-[4-(5-Chloro-2-methyl-phenyl)-6-methylamino-[1,3,5]-triazin-2-ylamino]-phenyl}-methanol; (S)-2-Amino-5-guanidino-pentanoic acid 4-[4-amino-6-(5-chloro-2-methyl-phenyl)-[1,3,5]triazin-2-ylamino]-benzyl ester; (S)-Pyrrolidine-2-carboxylic acid 4-[4-amino-6-(5-chloro-2-methyl-phenyl)-[1,3,5]triazin-2-ylamino]-benzyl ester; 2-Amino-propionic acid 4-[4-amino-6-(5-chloro-2-methyl-phenyl)-[1,3,5]-triazin-2-ylamino]-benzyl ester; 6-(5-Chloro-2-methyl-phenyl)-N-(4-methoxy-methyl-phenyl)-[1,3,5]triazine-2,4-diamine; 6-(5-Chloro-2-methoxy-phenyl)-N-p-tolyl-[1,3,5]triazine-2,4-diamine; 6-(2-Bromo-5-chloro-phenyl)-N-(4-chloro-phenyl)-[1,3,5]triazine-2,4-diamine; N-(4-Chloro-phenyl)-6-(2-chloro-5-trifluoromethyl-phenyl)-[1,3,5]triazine-2,4-diamine; 6-(2-chloro-5-methyl-phenyl)-N-(4-chloro-phenyl)-[1,3,5]triazine-2,4-diamine; [4-Chloro-6-(5-chloro-2-methyl-phenyl)-[1,3,5]triazin-2-yl]-(1H-indazol-5-yl)-amine; 6-(5-chloro-2-fluoro-phenyl)-N-(4-chloro-phenyl)-[1,3,5]triazine-2,4-diamine; 6-(2-bromo-5-methyl-phenyl)-N-(4-chloro-phenyl)-[1,3,5]triazine-2,4-diamine; 4-[4-Amino-6-(5-chloro-2-methyl-phenyl)-[1,3,5]triazin-2-ylamino]-benzaldehyde; N-(4-Chloromethyl-phenyl)-6-(5-chloro-2-methyl-phenyl)-[1,3,5]triazine-2,4-diamine; or physiologically acceptable salts thereof.

2. The method of claim 1 wherein the animal is a mammal.

* * * * *

UNITED STATES PATENT AND TRADEMARK OFFICE
CERTIFICATE OF CORRECTION

PATENT NO. : 7,291,616 B2
APPLICATION NO. : 10/285364
DATED : November 6, 2007
INVENTOR(S) : Rama Bhatt et al.

It is certified that error appears in the above-identified patent and that said Letters Patent is hereby corrected as shown below:

Column 82
Line 11, "-[13,5]" should read as -- -[1,3,5] --
Line 38, "(4-" should read as -- {4- --

Signed and Sealed this

Thirteenth Day of May, 2008

JON W. DUDAS
*Director of the United States Patent and Trademark Office*